US006589529B1

US 6,589,529 B1

(12) United States Patent
Choi et al.

(10) Patent No.: US 6,589,529 B1
(45) Date of Patent: Jul. 8, 2003

(54) ROTAVIRUS SUBUNIT VACCINE

(75) Inventors: Anthony Choi, Park Hills, KY (US); Richard L. Ward, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 09/429,801

(22) Filed: Oct. 29, 1999

Related U.S. Application Data

(60) Provisional application No. 60/106,347, filed on Oct. 30, 1998.

(51) Int. Cl.[7] .................. A61K 39/12; A61K 39/00; A61K 39/15
(52) U.S. Cl. .................. 424/186.1; 424/184.1; 424/185.1; 424/204.1; 424/215.1
(58) Field of Search .............. 424/184.1, 186.5, 424/204.1, 215.1, 185.1, 186.1

(56) References Cited

U.S. PATENT DOCUMENTS

| | | | |
|---|---|---|---|
| 4,341,763 A | 7/1982 | Zygraich | 424/89 |
| 4,624,850 A | 11/1986 | Albert et al. | 424/89 |
| 4,636,385 A | 1/1987 | Plotkin et al. | 424/89 |
| 4,704,275 A | 11/1987 | Wyatt et al. | 424/89 |
| 4,751,080 A | 6/1988 | Wyatt et al. | 424/89 |
| 4,927,628 A | 5/1990 | Chanock et al. | 424/89 |
| 5,374,426 A | 12/1994 | Sabara et al. | 530/403 |
| 5,474,773 A | 12/1995 | Ward | 424/184.1 |
| 5,620,896 A | 4/1997 | Hermann et al. | 435/320.1 |
| 5,626,851 A | 5/1997 | Clark et al. | 424/205.1 |
| 5,695,767 A | 12/1997 | Ward | 424/215.1 |
| 6,187,319 B1 * | 2/2001 | Hermann et al. | 424/215.1 |

FOREIGN PATENT DOCUMENTS

| | | |
|---|---|---|
| EP | 0 235 391 | 9/1987 |
| EP | 0 235 754 | 9/1987 |
| WO | 92/07941 | 5/1992 |

OTHER PUBLICATIONS

López et al., Mapping the subgroup epitopes of rotavirus protein VP6, Virology, vol. 204, pp. 153–162, 1994.*
Tang et al., Comparison of the rotavirus gene 6 from different species by sequences analysis and localization of subgroup–specific epitopes using site–directed mutagenesis, Virology, vol. 237, pp. 89–96, 1997.*
Newman et al., Saponin adjuvant induction of ovalbumin–specific CD8+ cytotoxic T lymphocyte responses, Journal of Immunology, vol. 148, No. 8, pp. 2357–2362, 1992.*
Kohli, et al. (1993) Epitope mapping of the major inner capsid protein of group A rotavirus using peptide synthesis. Virology194. 110–116.
McNeal, et al. (1998) Stimulation of local immunity and protection in mice by intramuscular immunization with triple–or double–layered rotavirus particles and QS–21. Virology 243. 158–166.

Courtesy Copy of International Search Report. (Apr. 4, 2000) 6 pages.
Agren, et al., "Adjuvanticity of the Cholera Toxin A1–Based Gene Fusion Protein, CTA1–DD, Is Critically Dependent on the ADP–Ribosyltransferase and Ig–Binding Activity", J. Immunology, 1999, 162; pp. 2432–2440.
Ausubel, et al., "Current Protocols in Molecular Biology", Eds., John Wiley & Sons, Inc. 1987 May 3, 2001.
Baños, et al., "Identification of a T–Helper Cell Epitope on the Rotavirus VP6 Protein", J. Virology, 71(1), Jan. 1997, pp. 419–426.
Choi, et al., "Particle–Bombardment–Mediated DNA Vaccination with Rotavirus VP4 or VP7 Induces High Levels of Serum Rotavirus IgG but Fails to Protect Mice against Challenge", Virology 250, pp. 230–240, 1998.
Choi, et al., "Particle–Bombardment–Mediated DNA Vaccination with Rotavirus VP6 Induces High Levels of Serum Rotavirus IgG but Fails to Protect Mice against Challenge", Virology 232, pp. 129–138, 1997.
Fernandez, et al., "Passive Immunity to Bovine Rotavirus in Newborn Calves Fed Colostrum Supplements from Cows Immunized with Recombinant SA11 Rotavirus Core–Like Particle (CLP) or Virus–Like Particle (VLP) Vaccines", Vaccines, vol. 16, No. 5, pp. 507–516, 1998.
Kapikian & Chanock, "Rotaviruses", Virology, Second Edition, Fields, et al., Eds., New York:Ravenpress, 1353–1404, 1990.
Mackow, et al., "Immunization with Baculovirus–Expressed VP4 Protein Passively Protects Against Simian and Murine Rotavirus Challenge", J. Virology, pp. 1698–1703, Apr. 1990.

(List continued on next page.)

Primary Examiner—Hankyel T. Park
Assistant Examiner—Stacy S. Brown
(74) Attorney, Agent, or Firm—Loy M. White; James J. Mullen, III

(57) ABSTRACT

The present invention is directed to the generation and use of recombinant rotavirus fusion proteins as immunogens to produce a protective immune response from immunized individuals. In one embodiment, the present invention contemplates a recombinant rotavirus fusion protein vaccine composition comprising a rotavirus subunit protein or immunogenic fragment thereof, and an adjuvant in combination with the recombinant rotavirus subunit fusion protein. In one aspect of this embodiment, the recombinant rotavirus fusion protein comprises a rotavirus subunit protein and a fusion partner protein in genetic association with the rotavirus subunit protein, wherein the fusion partner protein does not interfere with expression and immunogenicity of the rotavirus subunit protein, the fusion partner protein prevents complex formation by the rotavirus subunit protein, and the fusion partner protein facilitates purification of the recombinant rotavirus fusion protein. In another aspect of this embodiment, the rotavirus subunit protein is selected from the group consisting of VP1 VP2, VP3, VP4, VP6, VP7, NSP1, NSP2, NSP3, NSP4 or NSP5. In yet another aspect of this embodiment, the rotavirus subunit protein is VP6.

7 Claims, 7 Drawing Sheets

OTHER PUBLICATIONS

O'Neal, et al., "Rotavirus Virus–Like Particles Administered Mucosally Induce Protective Immunity", *J. Virology*, 71(11), pp. 8707–8717, Nov. 1997.

O'Neal, et al., "Rotavirus 2/6 Viruslike Particles Administered Intranasally with Cholera Toxin, *Escherichia coli* Heat–Labile Toxin (LT), and LT–R192G Induce Protection from Rotavirus Challenge", *J. Virology*, 72(4), pp. 3390–3393, Apr. 1998.

Smith, et al., Pediatrics, "Cost–effectiveness Analysis of a Rotavirus Immunization Program for the United States", 96(4), pp. 609–615, Oct. 1995.

Pérez–Schael, et al., "Efficacy of the Rhesus Rotavirus–Based Quadrivalent Vaccine in Infants and Young Children in Venezuela", New England Journal of Medicine, 337(17), pp. 1181–1187, Oct. 1997.

* cited by examiner

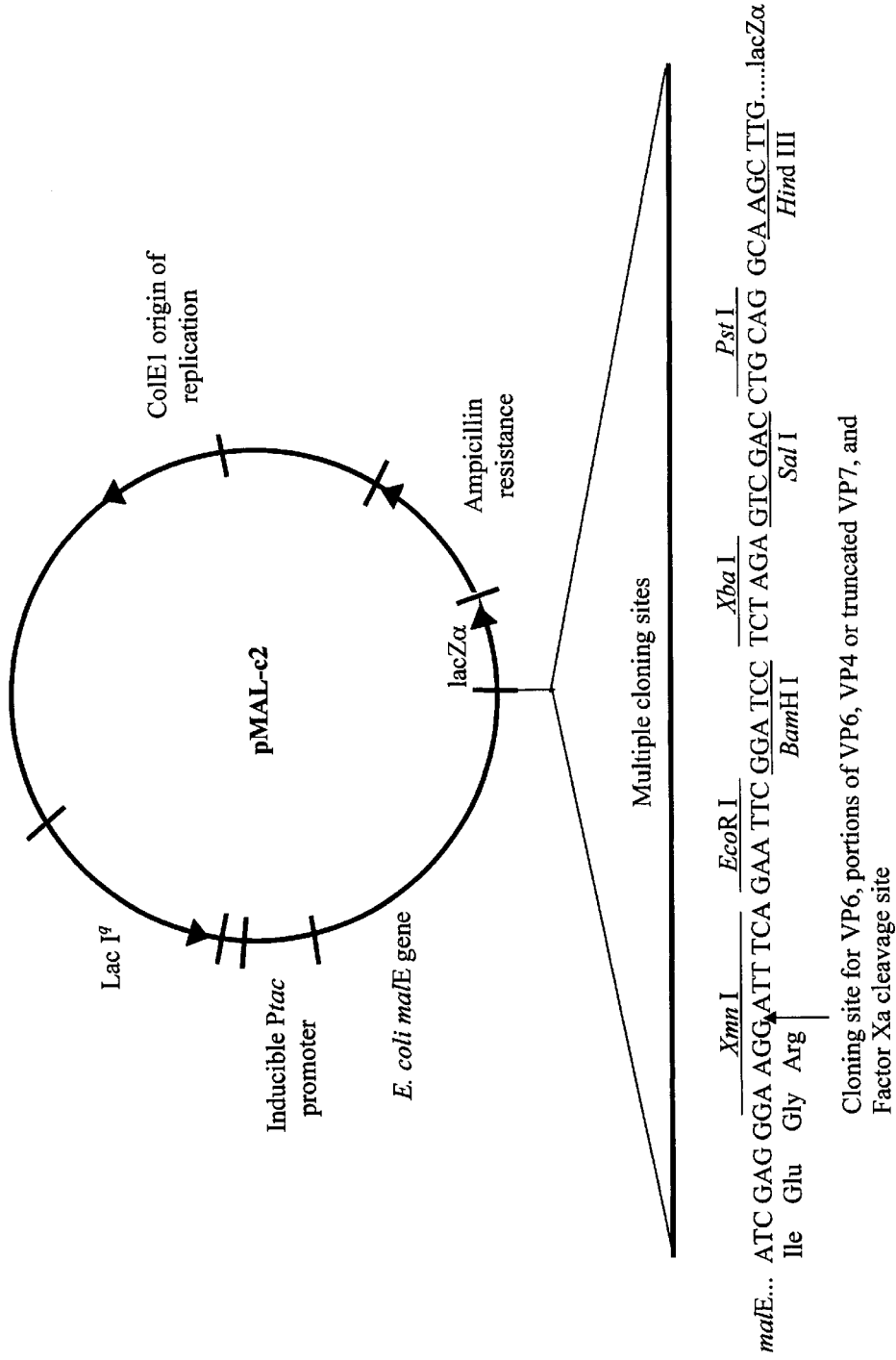
Figure 1. Plasmid map of pMAL-c2 used for expression of chimeric MBP proteins genetically fused to rotavirus proteins

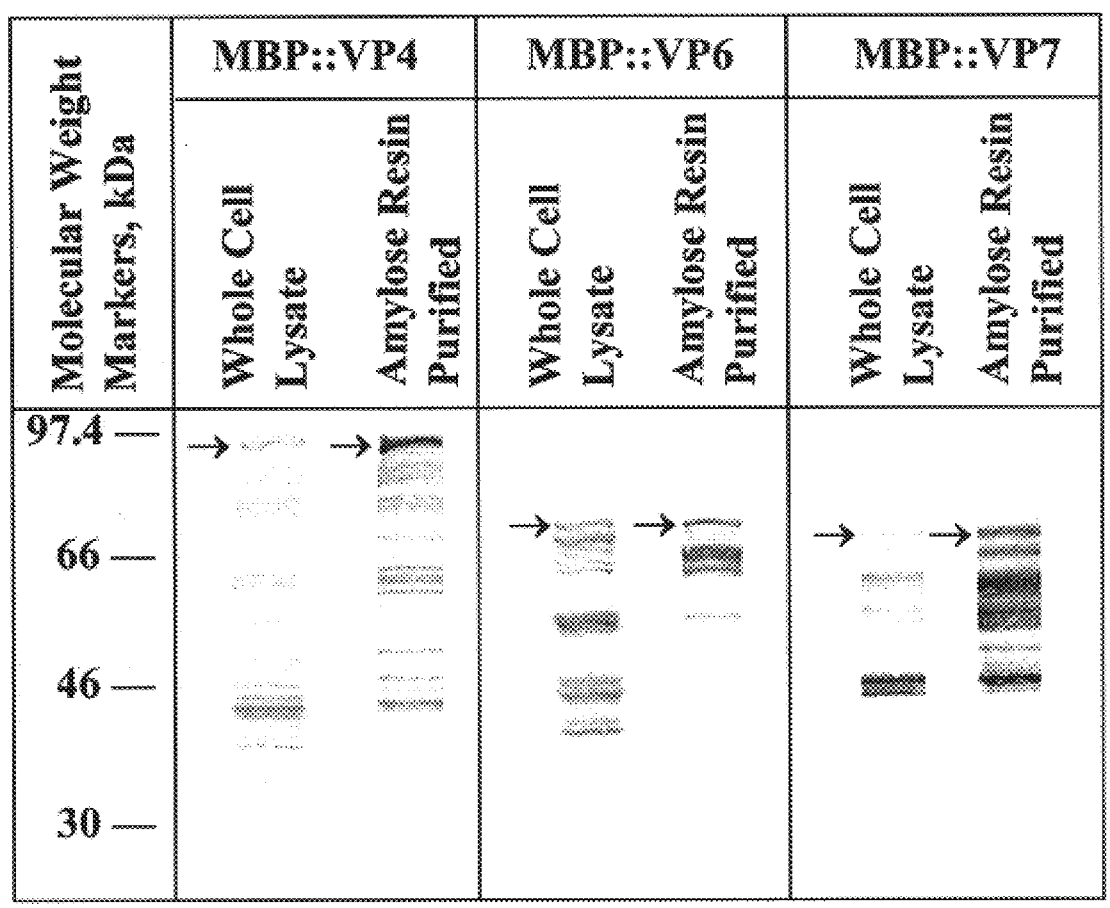
Figure 2. Western blot analyses of chimeric MBP protein genetically fused with rotavirus VP4, VP6 or a truncated VP7 protein

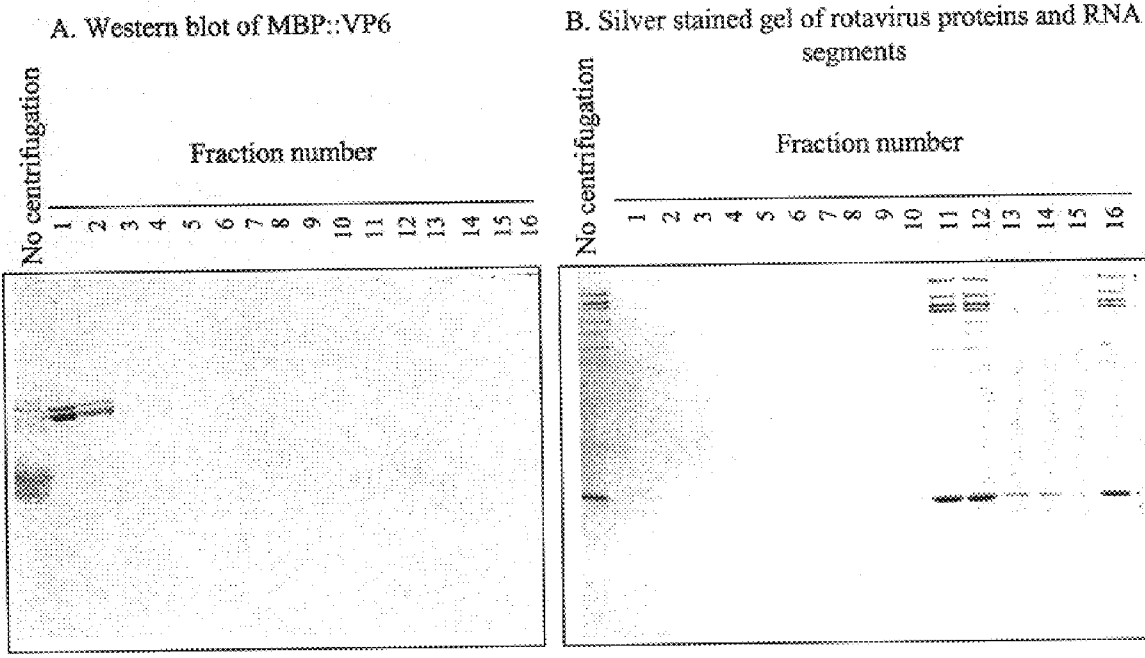
Figure 3. Western blot analyses of MBP::VP6 and silver stained gel of rotavirus particles in fractions collected after ultracentrifugation through a sucrose gradient

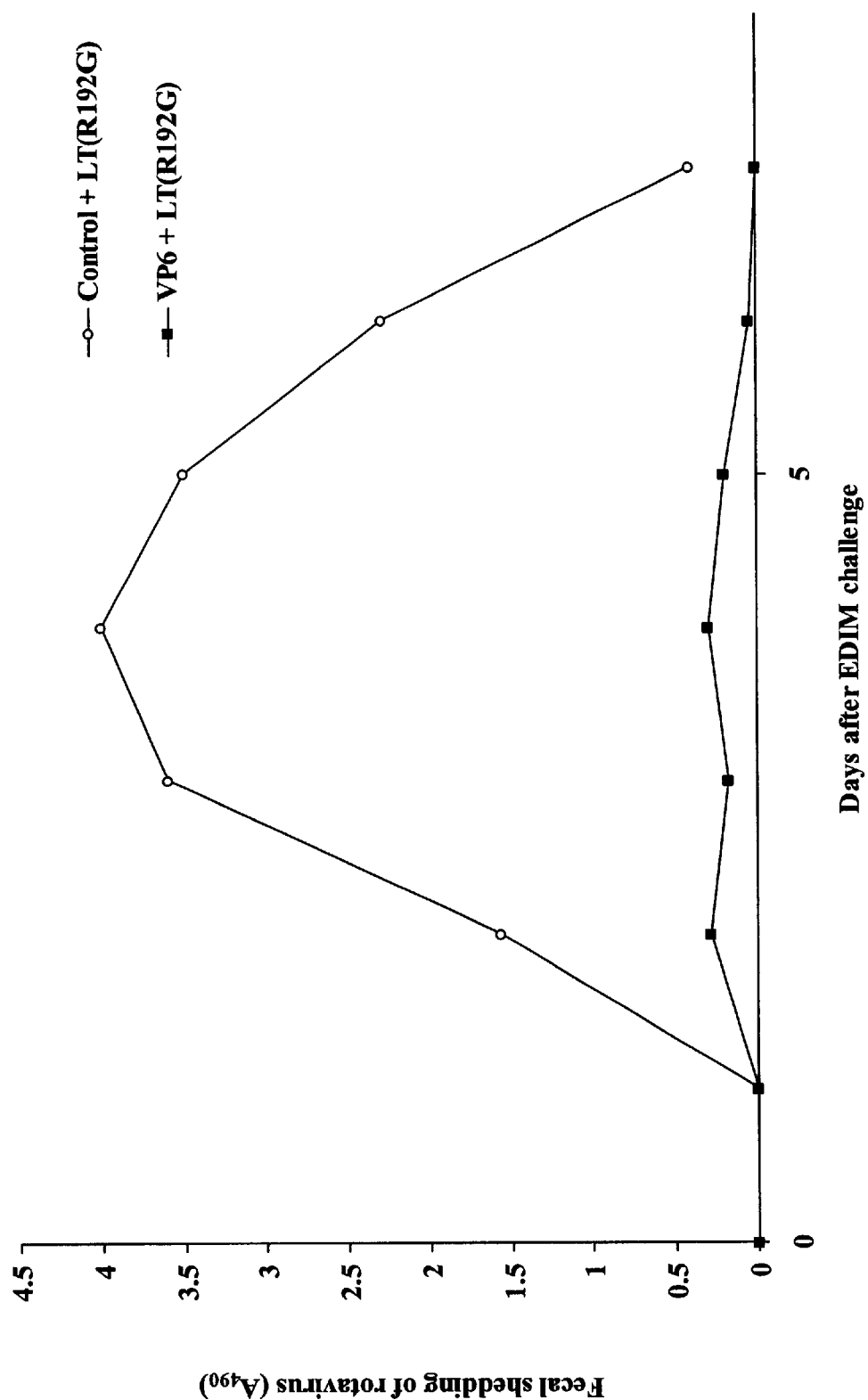
Figure 4. Intranasal VP6 + LT(R192G)

Figure 5. Regions of VP6 cloned into pMAL-c2. VP6 is delineated into regions A, B, C and D. pMAL-c2/EDIM6AB, encodes regions A and B, pMAL-c2/EDIM6BC encodes regions B and C, and pMAL-c2/EDIM6CD encodes regions C and D.

| Plasmid | Amino acids encoded |
|---|---|
| PMAL-c2/EDIM | 1-397 |
| PMAL-c2/EDIM6AB | 1-196 |
| PMAL-c2/EDIM6BC | 97-299 |
| PMAL-c2/EDIM6CD | 197-397 |

Regions of VP6: A, B, C, D

Figure 6. Western blot analyses of antisera collected from mice immunized with plasmids expressing chimeric MBP genetically fused with VP6$_{AB}$, VP6$_{BC}$, or VP6$_{CD}$
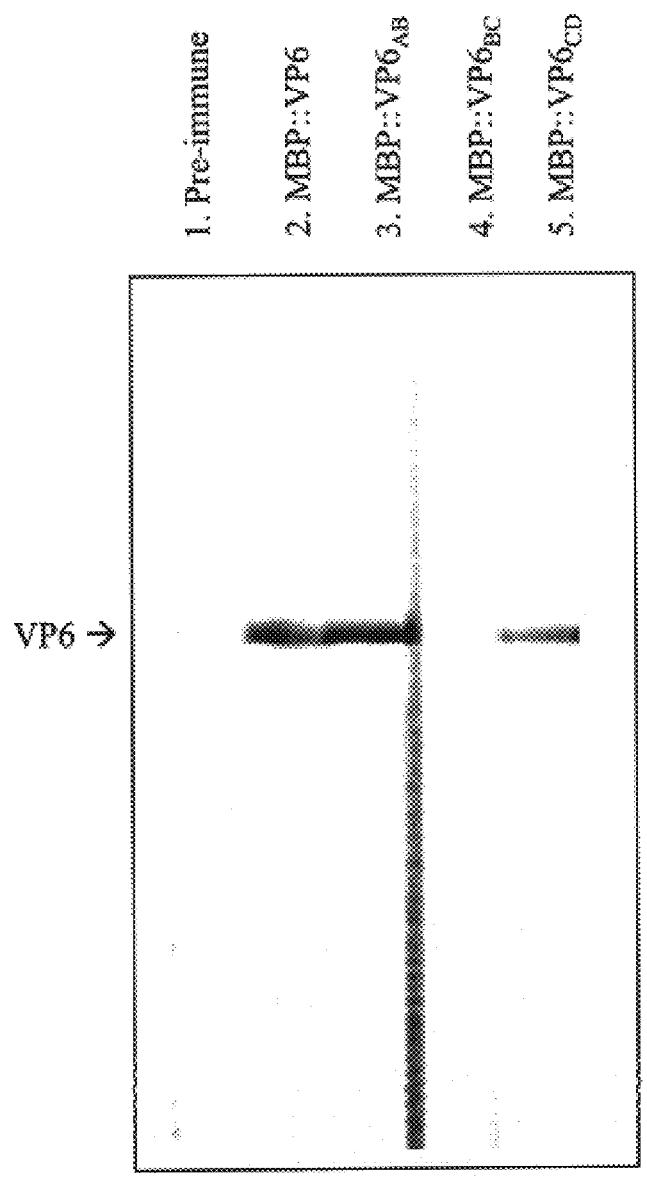

Figure 7. Regions of $VP6_{CD}$ cloned into pMAL-c2. The CD region of VP6 is delineated into subregions 1, 2, 3, and 4. These subregions were cloned into pMAL-c2 to create pMAL-c2/$EDIM6_{CD1}$, pMAL-c2/$EDIM6_{CD2}$, pMAL-c2/$EDIM6_{CD3}$, and pMAL-c2/$EDIM6_{CD4}$.

| Plasmids | Amino acids encoded |
|---|---|
| pMAL-c2/$EDIM6_{CD}$ | 197-397 |
| pMAL-c2/$EDIM6_{CD1}$ | 197-263 |
| pMAL-c2/$EDIM6_{CD2}$ | 244-310 |
| pMAL-c2/$EDIM6_{CD3}$ | 291-351 |
| pMAL-c2/$EDIM6_{CD4}$ | 332-397 |

Regions of VP6

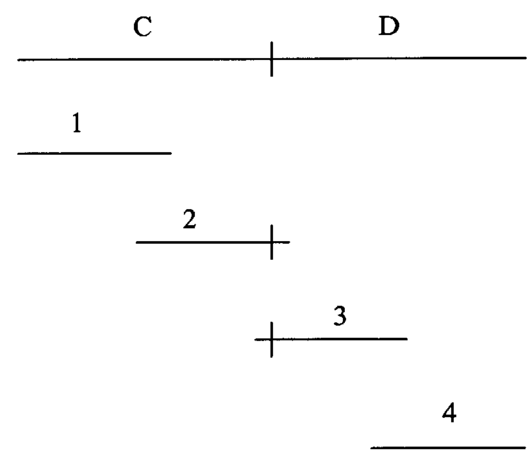

ROTAVIRUS SUBUNIT VACCINE

This application claims the benefit of provisional application Ser. No. 60/100,347 filed Oct. 30, 1998.

BACKGROUND OF THE INVENTION

Rotaviruses comprise a genus within the family Reoviridae, and are ubiquitous throughout the animal kingdom. Rotavirus infection is known to cause gastrointestinal disease and is considered the most common cause of gastroenteritis in infants. In fact, essentially every species of domestic animal tested has its own endogenous rotaviruses that cause diarrhea in newborns. Rotaviruses are also thought to be the most significant cause of gastroenteritis in young children and animals. Kapikian & Chanock, *Rotaviruses, Virology*, 2nd edition, Fields et al., eds., New York: Ravenpress, 1353 1404 (1990). Rotaviruses cause diarrheal disease primarily in the young, but infection and disease in older children and adults are also common.

Rotavirus infection is the leading cause of human diarrhea both in developed and developing countries, especially in infants less than one year of age. Worldwide approximately 870,000 children die of rotavirus associated disease every year in developing countries. Even in the United States there are approximately 70 deaths and 200,000 hospitalizations per year due to rotavirus diarrhea. While mortality has been controlled in developed countries by universal access to emergency medical care, morbidity from rotavirus disease remains high.

Around 90% of infants and children develop a rotavirus infection by the third year of life whether they are living in a developed or developing country. The impact of the disease is substantial. An estimated 3,000,000 cases of rotavirus diarrhea occur in the United States annually, leading to some 500,000 physician visits and 55,000–100,000 hospitalizations, which costs the health care system an estimated $500,000,000 to $600,000,000 a year. When indirect costs are included, the figure rises to $1.4 billion. *Pediatrics*, 609–615 (1995).

Rotaviruses are double-stranded RNA viruses and contain a multi-segmented genome. Because the viral genome is arranged in segments, these viruses are capable of genetic reassortment. This reassortment occurs when two or more rotaviruses infect a single cell and the various viral segments reassort during the packaging of new virus particles assembled in the cytoplasm of infected cells. The ability of the virus to reassort its genome components results in a great diversity of immune responses generated against the virus. This ability has also made generation of a rotavirus vaccine extremely challenging.

A variety of different approaches have been taken to generate a rotavirus vaccine suitable to protect human populations from the various serotypes of rotavirus. These approaches include various Jennerian approaches, use of live attenuated viruses, use of virus-like particles, nucleic acid vaccines and viral sub-units as immunogens.

An example of a Jennerian vaccine can be found in Zygraich, U.S. Pat. No. 4,341,763, issued Jul. 27, 1982, entitled, "Methods of Vaccinating Humans Against Rotavirus Infection." In this reference, bovine rotaviruses, either attenuated or inactivated, were used to immunize human beings against rotavirus infection. A modified Jennerian approach has also been adopted with the goal of attaining broader antigenic coverage. This approach entailed engineering new reassortant rotavirus types so that a group of viruses would simultaneously display epitopes of various serotypes. However, as with all attenuated viruses, there is always a high risk of reversion.

The Food and Drug Administration has recently approved a multivalent vaccine against rotavirus making it available to pediatricians in the United States. The vaccine, which was developed by Albert Z. Kapikian, MD, and colleagues at the Laboratory of Infectious Diseases (NIAID) is an excellent example of a multivalent vaccine. A recent reported study conducted in Caracas testing this vaccine was reported in the New England Journal of Medicine 1997; 337, 1181–1187. Among some 2,200 infants enrolled in the double-blind, placebo controlled study, the vaccine was successful in reducing severe diarrheal illness in about 70% of subjects but was less effective at reducing the incidence of less serious diarrheal illness. Recently, it was reported that there have been serious side effects such as bowel blockage associated with this vaccine.

Another example of the modified Jennerian approach is found in Clark et al., U.S. Pat. No. 5,626,851, issued May 6, 1997, entitled, "Rotavirus Reassortant Vaccine." In this example a rotavirus reassortant suitable for use as a vaccine was produced using genetic reassortment between an attenuated bovine rotavirus and at least one rotavirus representing an epidemiologically important serotype. This reference looked to create a bovine rotavirus that carried either VP4 or VP7 genes which, when presented to a immunologically naive subject, would induce a protective immune response therein. Thus, this method relies upon the use of whole viruses to immunize a subject.

U.S. Pat. Nos. 4,624,850, 4,636,385, 4,704,275, 4,751,080, 4,927,628, 5,474,773, and 5,695,767, each describe a variety of rotavirus vaccines and/or methods of preparing the same. A commonality shared by the members of this group is that each of these vaccines relies on the use of whole viral particles to create the ultimate rotavirus vaccines. Given the long standing need for an effective, multivalent vaccine, it is clear that this body of work has been only partially successful in addressing the need for such a vaccine.

Departing from traditional methods of vaccine generation, advances in the field of molecular biology have permitted the expression of individual rotavirus proteins. Using these techniques, vaccine candidates generated from virus-like particles of different protein compositions have shown potential as subunit vaccines. In one reference, VLPs containing VPs 2 and 6 or VPs 2, 6, and 7 were administered to mice with and without the addition of cholera toxin. O'Neal et al., "Rotavirus Virus-like Particles Administered Mucosally Induce Protective Immunity," *J. Virology*, 71(11):8707–8717 (1997). Both types of VLPs induced protective immunity in immunized mice, although protection was more effective when the VLPs were administered with cholera toxin (CT). In a subsequent study by the same group, the *Escherichia coli* heat-labile toxin (LT) was compared to CT for effectiveness in producing rotavirus protection. O'Neal et al., "Rotavirus 2/6 Virus-like Particles Administered Intranasally with Cholera Toxin, *Escherichia coli* Heat-Labile Toxin (LT), and LT-R192G Induce Protection from Rotavirus Challenge," *J. Virology*, 72(4):3390–3393 (1998). This group concluded that both the wild-type LT and a recombinant form of the molecule were effective adjuvants when immunizing with rotavirus VLPs.

Core-like particles and VLPs have also been used to immunize cows. Fernandez, et al., "Passive Immunity to Bovine Rotavirus in Newborn Calves Fed Colostrum Supplements From Cows Immunized with Recombinant SA11 rotavirus core-like particle (CLP) or virus-like particle (VLP) vaccines," *Vaccine*, 16(5):507–516 (1998). In this study the ability of CLPs and VLPs to create passive immunity was studied. This group concluded that VLPs were more effective than CLPs in inducing passive immunity.

In several studies the individual viral proteins have also been used to immunize subjects. For example, one group used bacculovirus-expressed VP4 protein from the simian rhesus rotavirus (RRV) to parenterally immunize murine dams. Newborn mice suckling from immunized dams were found to be protected against RRV challenge and against challenge by a murine rotavirus through a passive immunity scheme. Mackow et al., "Immunization with bacculovirus-Expressed VP4 Protein Passively Protects Against Simian and Murine Rotavirus Challenge," *J. Virol.* 64(4): 1698–1703 (1990).

Rotavirus proteins have even been used as immunological carrier complexes to facilitate the presentation of other epitopes to a subject. In one reference, VP6 was chosen as a carrier molecule for a particular antigen, based on the viral protein's ability to bind peptides. Sabara, et al., U.S. Pat. No. 5,374,426, issued Dec. 20, 1994, entitled, "Rotavirus Nucleocapsid Protein VP6 in Vaccine Compositions."

Exploiting another avenue, research has also been performed where a protective immune response was elicited using a DNA vaccine. Herrmann, et al., U.S. Pat. No. 5,620,896, issued Apr. 15, 1997, entitled, "DNA Vaccines Against Rotavirus Infections." While the results from this method are interesting, the degree of protection found in mice immunized with plasmids containing either the VP4, VP7 or VP6 genes in a murine retrovirus were very limited. Moreover, there are at least two reports of rotavirus DNA vaccines that failed to provide any protection to the immunized animal from rotaviral infection. Choi, et al., "Particle Bombardment-Mediated DNA Vaccination with Rotavirus VP6 Induces High Levels of Serum Rotavirus IgG but Fails to Protect Mice Against Challenge," *Virology* 232: 129–138 (1997). Choi et al. "Particle Bombardment-Mediated DNA Vaccination With Rotavirus VP4 or VP7 Induces High Levels of Serum IgG but Fails to Protect Mice Against Challenge," *Virology* 250:230–240 (1998).

This review of the state of the art attempts to provide some measure of the extent of time and energy that has been expended to date to develop an effective rotavirus vaccine. Yet, even with the most successful efforts to date, even the severe forms of rotaviral disease can be prevented only bout 75% of the time. Given this limitation, there remains a need for a safe and effective rotavirus vaccine, which overcomes the above deficiencies. The vaccine of present invention is designed to remedy and eliminate these problems.

SUMMARY OF THE INVENTION

The invention disclosed herein relates to compositions comprising various rotaviral proteins and methods of using these compositions to provide protection against rotaviral disease. One embodiment of the invention is a composition comprising a rotavirus VP6 protein or a fragment thereof, and an adjuvant in a pharmaceutical carrier, wherein said adjuvant is effective in generating a disease-reducing response to said VP6 protein.

Another embodiment of the invention encompasses a recombinant rotavirus fusion protein composition, comprising: a rotavirus subunit fusion protein or fragment thereof, a fusion protein partner in genetic association with said recombinant rotavirus subunit protein or fragment thereof, and an adjuvant in a pharmaceutical carrier, wherein said adjuvant is effective in stimulating a disease-reducing immunogenic response to said rotavirus fusion protein.

A full-length DNA copy of a gene encoding a recombinant rotavirus fusion protein, wherein said gene encoding said recombinant rotavirus protein comprising a rotavirus subunit protein or an immunogenic fragment thereof, and a fusion partner protein is contemplated in another embodiment of the invention disclosed herein.

A host cell comprising a DNA clone encoding recombinant rotavirus proteins is contemplated in another embodiment of the disclosed invention.

The invention disclosed also contemplates a computer readable medium having recorded thereon peptide sequences of rotavirus proteins selected from the group consisting of SEQ ID NOs:15–25.

A number of methods are disclosed as part of the invention. For example, one embodiment discloses a method of generating an immune response in a subject in need of rotavirus immunity comprising the steps of administering an immunogenic composition of comprising a rotavirus protein or fragment thereof, and an adjuvant in a pharmaceutically acceptable form to said subject and generating a disease-reducing immunogenic response in said subject.

Another embodiment of the invention is a method of immunizing a subject in need of rotavirus immunity comprising the steps of: immunizing with a rotavirus vaccine; and subsequently immunizing said subject with a recombinant rotavirus vaccine composition, whereby immunological protection of said individual against rotavirus infection is increased.

BRIEF DESCRIPTION OF THE DRAWINGS

FIG. 1 shows some of the important features of pMAL-c2. Using this plasmid, recombinant plasmids were constructed which express chimeric proteins containing, the entire VP6, portions of VP6, the entire VP4 or a truncated form of VP7. pMAL-c2 contains a promoter sequence called Ptac which controls transcription of the fusion gene malE-lac Zα. The gene malE-lac Zα encodes a chimeric protein containing MBP and the a fragment of the enzyme β-galactosidase. Rotavirus gene sequences were cloned into Xmn I, which is one of the multiple restriction sites present in the plasmid used for gene cloning. The created recombinant plasmids express chimeric proteins containing rotavirus proteins that are genetically fused with MBP. The precise site for Xmn I insertion is indicated by the arrow in FIG. 1. The same arrow also marks the exact position in the protein which can be enzymatically digested by Factor Xa in some, but not all, chimeric MBP proteins. pMAL-c2 also contains the lac Iq sequence which encodes a repressor protein that suppresses Ptac controlled transcription until IPTG is added. The plasmid also contains the colE1 origin of replication in *E. coli* and the ampicillin resistance gene that are typical features of many bacterial plasmids.

FIG. 2 shows the results of Western blot analysis of chimeric MBP proteins, which contain MBP genetically fused with various rotavirus proteins. Aliquots of the purified proteins were subjected to separation by SDS-PAGE. Western blot analyses were then carried out by blotting separated proteins onto nitrocellulose sheets. Antibodies generated against MBP were used and a chromogenic reaction was performed to visualize chimeric proteins derived from unfractionated cells (whole cell lysate) before the first step and purified proteins after the last step of the purification scheme. The arrows indicate the chimeric proteins containing MBP genetically fused with VP4, VP6 or truncated VP7.

FIG. 3 shows evidence to establish that chimeric MBP::VP6 protein does not form structures that resemble rotavirus-like particles. Purified MBP::VP6 was put on the top of a sucrose gradient which was layered on top of a cesium chloride cushion. Rotavirus particles that were devoid of VP4 and VP7 were also layered on an identical sucrose gradient/cesium chloride cushion. By subjecting the protein and virus particles to a centrifugal force, the majority of the rotavirus particles traversed into fraction number 11 and 12 of the sucrose gradient and into fraction number 16 containing cesium chloride. In contrast, chimeric NBP::VP6 did not traverse into the gradient but remained in the top fractions (number 1 and 2). These results clearly demonstrated that the presence of MBP in the fusion protein does not allow MBP::VP6 to form any structures that resemble rotavirus particles.

FIG. 4. Rotavirus shedding in BALB/c immunized with MBP::VP6 and LT (attenuated E. coli heat labile toxin) or LT only following challenge with EDIM. Groups of 8 BALB/c mice were intranasally immunized with two doses, separated by 14 days, of either 8.8 ug MBP::VP6 and 10 μg of LT or 10 μg of LT alone. Four weeks after the last immunization, the mice were challenged with $4 \times 10^4$ focus forming units (ffu) of EDIM (P9 12/15/97). Stools were collected for seven days following challenge and were tested for rotavirus antigen by enzyme-linked immunosorbent assay (EIA). The $A_{490}$ values are the averages obtained each day.

FIG. 5 illustrates the region of VP6, which may assist in creating minimal subunit rotavirus vaccines. VP6, which consist of 397 amino acid residues, was delineated into four regions: regions A, B, C and D. The exact amino residues delineated by these regions were indicated. The gene sequences that encode regions A and B, B and C, or C and D were cloned into pMAL-c2 at the Xmn I site. The plasmids were given the names pMAL-c2/EDIM$_{AB}$, pMAL-c2/EDIM$_{BC}$ and pMAL-c2/EDIM$_{CD}$ respectively.

FIG. 6 provides evidence that mice inoculated with chimeric MBP proteins containing regions A and B or containing regions C and D generated IgG which specifically recognized VP6. In these experiments, rotavirus particles were subjected to SDS-PAGE. The separated proteins were then transferred to nitrocellulose sheets. The sheets were cut into strips. Individual strips were incubated with a specific immune serum sample collected from mice inoculated with pMAL-c2/EDIM$_{AB}$, pMAL-c2/EDIM$_{BC}$ or pMAL-c2/EDIM$_{CD}$. While pMAL-c2/EDIM$_{AB}$- and pMAL-c2/EDIM$_{CD}$-inoculated mice generated anti-VP6 IgG, no specific IgG was detected by pMAL-c2/EDIM$_{BC}$-immunized mice.

FIG. 7 further defines the CD region of VP6 in order to determine whether an even smaller minimal subunit rotavinis vaccine can be attained. The CD region was delineated into four regions: regions 1, 2, 3 and 4. The exact amino residues delineated by these regions were indicated. Recombinant plasmids were constructed using pMAL-c2 to harbor regions 1, 2, 3, and 4. The plasmids were given the names pMAL-c2/EDIM$_{CD1}$, pMAL-c2/EDIM$_{CD2}$, pMAL-c2/EDIM$_{CD3}$ and pMAL-c2/EDIM$_{CD4}$ respectively.

DETAILED DESCRIPTION OF THE PREFERRED EMBODIMENT

This invention relates to the generation of rotavirus subunit proteins for use in vaccines and methods of providing protective immunity to vertebrates, including humans, against rotavirus infection or disease. As one embodiment, the protective immunity generated by vaccines containing the recombinant rotavirus proteins of the present invention is a dominantly cell-mediated immune response. This immune response may interfere with the infectivity or activity of the rotavirus, or it may limit the spread or reproduction of the virus. The immune response resulting from vaccination with a vaccine containing the proteins of the present invention provides protection against subsequent challenge by a homologous or heterologous rotavirus.

The vaccines of the present invention are composed of a native recombinant rotavirus protein or immunogenic fragment(s) thereof, a rotavirus fusion protein, or immunogenic fragment(s) thereof, an adjuvant, and a pharmaceutically acceptable carrier. According to one embodiment of the present invention, a composition comprising a rotavirus protein or an immunogenic portion thereof is genetically associated with a fusion protein partner, and an adjuvant such as the A1 subunit, the B subunit of cholera toxin or E. coli heat-labile toxin present in a pharmaceutically acceptable carrier. This composition is administered to an individual in whom an immune response directed against the rotavirus subunit protein is sought and protection against rotavirus infection and disease is desired.

The rotavirus native recombinant, or fusion proteins of the present invention may be composed of any rotavirus protein product or immunogenic fragment thereof. The rotavirus protein may be chosen from any of the structural or non-structural viral proteins encoded by the rotavirus genome. For example, in one embodiment, the rotavirus protein or immunogenic fragment thereof may be chosen by selecting from the group of rotavirus genome segments consisting of segment 1, 2, 3, 4, 5, 6, 7, 8, 9, 10, or 11, that encode rotavirus protein sequences. In another embodiment, the rotavirus protein or immunogenic fragment thereof may be selected from the group of rotavirus structural proteins consisting of VP1, VP2, VP3, VP4, VP6 and VP7. In another embodiment, the rotavirus protein may be selected from the group of rotavirus non-structural proteins consisting of NSP1, NSP2, NSP3, NSP4 and NSP5. In yet another embodiment, the rotavirus protein used in the fusion protein construct is VP6. In still another embodiment, the use of an immunogenic fragment of VP6 may be used in the present invention.

The rotavirus recombinant native or fusion proteins of the present invention may be used in a vaccine composition at a concentration effective to elicit an immune response from an immunized subject. The concentration of rotavirus proteins of the present invention may range from about 0.01 μg/ml to 1 mg/ml. In another embodiment, the concentration of rotavirus proteins used in a vaccine composition may range from about 0.1 μg/ml to 100 μg/ml. In yet another embodiment, the concentration of rotavirus proteins used in a vaccine composition may range from about 1.0 μg/ml to 10 μg/ml. In still another embodiment, the concentration of rotavirus proteins used in a vaccine composition may be about 8.8 μg/ml. These ranges are provided for the sake of guidance in practicing the present invention. It should be noted that other effective concentrations of recombinant rotavirus proteins may be determined by one of ordinary skill in the art using experimental techniques well known in that art.

The rotavirus fusion proteins contemplated by the present invention are composed of a suitable fusion protein partner in genetic association with a rotavirus protein or immunogenic fragment thereof. The term in genetic association refers to a contiguous sequence of amino acids produced from a mRNA produced from a gene containing codons for the amino acids of the rotavirus protein and the fusion protein partner. A suitable fusion protein partner consists of a protein that will either enhance or at least not diminish the recombinant expression of the rotavirus fusion protein product when the two are in genetic association. Further, a suitable fusion protein partner may actively prevent the assembly of the rotavirus fusion proteins into multimeric forms after the rotavirus fusion protein has been expressed. For example, the fusion protein partner should prevent the formation of dimers, trimers or virus-like structures that might spontaneously form if the rotavirus protein were recombinantly expressed in the absence of the fusion protein partner. Still further, a suitable fusion partner will facilitate the purification of the chimeric rotavirus fusion protein. A representative list of suitable fusion protein partners includes maltose binding protein, poly-histidine segments capable of binding metal ions, inteine, antigens to which antibodies bind, S-Tag, glutathione-S-transferase, thioredoxin, β-galactosidase, nonapeptide epitope tag from influenza hemagglutinin, a 11-amino acid epitope tag from vesicular stomatitis virus, a 12-amino acid epitope from the heavy chain of human Protein C, green fluorescent protein, cholera holo toxin or its B subunit, $E.$ $coli$ heat-labile holotoxin or its B subunit, CTA1-DD, streptavidin and dihydrofolate reductase.

The invention is also directed toward producing rotavirus proteins for use in vaccines directed to protect immunized individuals from rotavirus infection and/or disease. Accordingly, the invention contemplates the use of an adjuvant, such as an immunogenic protein, effective to induce desirable immune responses from an immunized animal. Such a protein mast possess those biochemical characteristics required to facilitate the induction of a protective immune response from immunized vertebrates while simultaneously avoiding toxic effects to the immunized animal.

In one embodiment of the present invention, rotavirus recombinant native or fusion proteins are mixed with an adjuvant such as a bacterial toxin. The bacterial toxin may be a cholera toxin. Alternatively, the rotavirus fusion protein may be mixed with the B subunit of cholera toxin (CTB). In another embodiment, an $E.$ $coli$ toxin may be mixed with the rotavirus fusion protein. For example, the rotavirus fusion protein may be mixed with $E.$ $coli$ heat-labile toxin (LT). The rotavirus fusion proteins of the present invention may be mixed with the B subunit of $E.$ $coli$ heat-labile toxin (LTB) to form a vaccine composition. Other adjuvants such as cholera toxin, labile toxin, tetanus toxin or toxoid, poly[di (carboxylatophenoxy)phosphazene] (PCPP), saponins Quil A, QS-7, and QS-21, RIBI (HAMILTON, Mont.), monophosphoryl lipid A, immunostimulating complexes (ISCOM), Syntax, Titer Max, M59, CpG, dsRNA, and CTA1-DD (the cholera toxin A1 subunit (CTA1) fused to a dimer of the Ig-binding D-region of Staphylococcus aureus protein A (DD)), are also contemplated.

The adjuvants discussed above may be used in a vaccine composition at a concentration effective to assist in the eliciting of an immune response against the recombinant rotavirus fusion proteins of the present invention from an immunized subject. The concentration of adjuvant included in the vaccine compositions of the present invention may range from about 0.01 $\mu$g/ml to 1 mg/ml. In another embodiment, the concentration of adjuvant used in a vaccine composition may range from about 0.1 $\mu$g/ml to 100 $\mu$g/ml. In yet another embodiment, the concentration of adjuvant used in a vaccine composition may range from about 1.0 $\mu$g/ml to 100 $\mu$g/ml. In still another embodiment, the concentration of adjuvant used in a vaccine composition may be about 10.0 $\mu$g/ml. These ranges are provided for the sake of guidance in practicing the present invention. It should be noted that other effective concentrations of adjuvants may be determined by one of ordinary skill in the art using experimental techniques well known in that art.

The invention also contemplates immunization with a rotavirus fusion protein, a recombinant native protein, or a fragment or fusion fragment, and a suitable adjuvant contained in a pharmaceutically acceptable composition. Such a composition should be sterile, isotonic, and provide a non-destabilizing environment for the rotavirus fusion protein and the adjuvant. Examples of this are buffers, tissue culture media, various transport media and solutions containing proteins (such as BSA), sugars (sucrose) or polysaccharides.

The vaccine compositions of the invention contain conventional pharmaceutical carriers. Suitable carriers are well known to those of skill in the art. These vaccine compositions may be prepared in liquid unit dose forms. Other optional components, e.g., stabilizers, buffers, preservatives, excipients and the like may be readily selected by one of skill in the art. However, the compositions may be lyophilized and reconstituted by the individual administering the vaccine prior to administration of the dose. Alternatively, the vaccine compositions may be prepared in any manner appropriate for the chosen mode of administration, e.g., intranasal administration, oral administration, etc. The preparation of a pharmaceutically acceptable vaccine, having due regard to pH, isotonicity, stability and the like, is within the skill of the art.

The dosage regimen involved in a method for vaccination, including the timing, number and amounts of booster vaccines, will be determined considering various hosts and environmental factors, e.g., the age of the patient, time of administration and the geographical location and environment.

Also included in the present invention are methods of vaccinating humans against rotavirus infection and disease with the novel rotaviral proteins and vaccine compositions described above. The vaccine compositions, comprising a full-length rotavirus protein, a rotavirus fusion protein, a recombinant native protein or fragments and fusion fragments, mixtures of the above, and an adjuvant described herein may be administered by a variety of routes contemplated by the present invention. Such routes include intranasal, oral, rectal, vaginal, intramuscular, intradermal and subcutaneous administration.

Vaccine compositions for parenteral administration include sterile aqueous or non-aqueous solutions, suspensions or emulsions, the protein vaccine, and an adjuvant as described herein. The composition may be in the form of a liquid, a slurry, or a sterile solid which can be dissolved in a sterile injectable medium before use. The parenteral administration is preferably intramuscular. Intramuscular inoculation involves injection via a syringe into the muscle. This injection can be via a syringe or comparable means. The vaccine composition may contain a pharmaceutically acceptable carrier. Alternatively, the present vaccine compositions may be administered via a mucosal route, in a suitable dose, and in a liquid form. For oral administration, the vaccine composition can be administered in liquid, or solid form with a suitable carrier.

Doses of the vaccine compositions may be administered based on the relationship between the concentration of the rotavirus fusion protein contained in the vaccine composition and that concentration of fusion protein required to elicit an immune response from an immunized host. The calculation of appropriate doses to elicit a protective immune response using the rotavirus fusion protein vaccine compositions of the present invention are well known to those of skill in the art.

A variety of immunization methods are contemplated by the invention to maximize the efficacy of the rotavirus protein vaccine compositions described herein. In one embodiment, females of offspring-bearing age are immunized with the vaccines of the invention. In this embodiment, immunized females develop a protective immune response directed against rotavirus infection or disease and then passively communicate this protection to an offspring by nursing. In another embodiment, newborns are immunized with the vaccine compositions of the invention and shortly thereafter the nursing mother is immunized with the same vaccine. This two tiered approach to vaccination provides the newborn with immediate exposure to viral epitopes that may themselves be protecting. Nevertheless, the passive immunity supplied by the mother would augment the protection enjoyed by the offspring. This method would therefore provide the offspring with both active and passive protection against rotavirus infection of disease.

In still another embodiment, an individual is immunized with the vaccine composition of the invention subsequent to immunization with a multivalent vaccine. The immunization of a subject with two different vaccines may synergistically act to increase the protection an immunized individual would enjoy over that obtained with only one vaccine formulation. One draw back of immunization with a multivalent live virus vaccine formulation is that booster immunizations with the same vaccine are usually not effective. In this embodiment of the invention, the vaccine compositions serve as such a booster to increase the protection of the immunized individual against rotaviral infection or disease.

The following examples teach the generation of all types of rotavirus protein vaccine compositions. These examples are illustrative and are not intended to limit the scope of the present invention. One of skill in the relevant art would be able to use the teachings described in the following examples to practice to full scope of the present invention.

EXAMPLES

Example 1

Construction of Recombinant pMAL-c2 Plasmids

Recombinant plasmids pMAL-c2/EDIM4, pMAL-c2/EDIM6 and pMAL-c2/LDIM7 were constructed using pMAL-c2 (New England Biolabs, Beverly Mass.) by insertion of cDNAs encoding full length VP4 or VP6, or a truncated form of VP7 (TrVP7) of rotavirus strain EDIM (FIG. 1). cDNAs were synthesized by polymerase chain reaction (PCR) using the plasmids pGEM-3Z/EDIM4, pGEM-3Z/EDIM6 and pGEM-3Z/EDIM7 as templates and gene specific primers determined by nucleotide sequencing of the gene inserts. The nucleotide sequences have been deposited into GenBank nucleotide sequence database and assigned with the Accession Numbers AF039219, U65988 and AF039220 for VP4, VP6 and VP7 gene respectively.

The murine EDIM strain of rotavirus used for the construction of the pGEM recombinant plasmids was originally isolated from the stool of an infected mouse and adapted to grow in cell culture by passage in MA-104 cells in the laboratory. A triply plaque-purified isolate of the ninth passage was used to infect MA-104 cells to yield stock virus for RNA purification. To generate cDNAs of rotavirus genes encoding strain VP4, VP6 and VP7, reverse transcription/polymerase chain reaction was carried out using purified genomic rotavirus RNA, a forward and a reverse primer obtained from the untranslatable regions of the gene. The cDNAs generated by RT/PCR were cloned into the Sma I site of the multiple cloning site of pGEM-3Z (Promega, Madison, Wis.). Ligation products were then transformed into E. coli. White transformants carrying recombinant plasmids were selected by growing cells on LB agar plates containing IPTG (0–5 mM) and X-gal. Plasmids from individual colonies were purified and were analyzed by nucleotide sequencing.

The cDNAs generated by PCR were inserted into the restriction site Xmn I of pMAL-c2, placing the inserted sequences downstream from and in genetic association with the E. coli malE gene, which encodes maltose binding protein (MBP), resulting in the expression of MBP fusion protein. The plasmid utilized the strong "tac" promoter and the malE translation initiation signals to give high-level expression of the fusion protein. pMAL-c2 contains the factor Xa cleavage site that is located downstream from the malE sequence to enable cleavage of the heterologous protein from MBP. The plasmid conveyed ampicillin resistance to recombinant bacteria and a lacZ-alpha gene sequence for blue-to-white selection of recombinants with inserts.

Following ligation of cDNA and XmnI-digested pMAL-c2, recombinant pMAL-c2 plasmids were transformed into E. coli. White colonies of bacteria containing recombinant plasmids on an agar plate were then identified in the presence of IPTG and X-gal, and selected for further screening by PCR for gene identity and orientation. Nucleotide sequencing was used to ultimately confirm the authenticity of the rotavirus gene sequence.

Example 2

Expression and Purification of Fusion Proteins

Recombinant bacteria were grown as an overnight culture (37° C., shaken at 215 rpm) in rich broth (tryptone, 10 gm; yeast extract, 5 NaCl, 5 gm; glucose, 2 gm and 100 mg of ampicillin per liter). On the following day, 10 ml of overnight cell culture were inoculated into 1 liter of rich broth containing glucose and ampicillin. The culture was grown until the optical density $A_{600}$ reached 0.6. IPTG was then added to 0.3 mM to induce expression of fusion protein. Growth was continued for 3 hours.

Cells were harvested by centrifugation (4,000 g; 20 min at 4° C.), resuspended in PBS, and subjected to centrifugation. The pellet was frozen at −20° C., thawed slowly in cold water, and resuspended in a total of 50 ml of buffer L (5 mM $NaH_2PO_4$, 10 mM $Na_2HPO_4$, 30 mM NaCl, 10 mM 2-beta mercaptoethanol and 0.2% Tween 20, 1 mM PMSF, 25 mM benzamidine, and 200 mg/L of lysozyme). After digestion for 15 min at room temperature (rt), the suspension was sonicated by three 30 second bursts (BioSonic IV, 50% power setting) while placed in an ice/water bath. NaCl (26.5 mg/ml) and RNase A (5 µl of 10 mg/ml) were added to each 10 ml of sonicate which was then centrifuged (54,000 g, 30 min) to obtain a supernatant containing a crude preparation of fusion protein.

Fusion proteins in the crude preparation were purified by affinity chromatography. Amylose resin (New England Biolab, Beverly Mass.) was prepared by placing 25 ml of the packed resin in a 250 ml centrifuge tube and washed twice with eight volumes of buffer C (Buffer L containing 0.5 M NaCl). For each wash, the mixture was rocked for 30 min at 4° C., and the resin was recovered by centrifugation (2,100 g, 5 min). The supernatants, which contained the fusion proteins, were mixed with amylose resin for 2 hours in a 500 ml flask on a magnetic stirrer. After centrifugation (2,100 g, 5 min), the resin was recovered, then resuspended in 50 ml of buffer C, rocked for 30 min and finally centrifuged to recover the resin. The resin was washed in this manner for a total of 3 times and finally washed overnight with 500 ml of buffer C.

On the following day, the resin was recovered by centrifugation (2,100 g, 5 min) and resuspended in 50 ml of buffer D (50 mM Tris-HCl, pH 7.5; 50 mM NaCl; 1 mM EDTA; 10 mM 2-beta mercaptoethanol; 1 mM PMSF), and rocked for 30 min. The resin was spun down and the bound fusion proteins were eluted from the resin with 250 ml of 15 mM maltose in buffer D for 2 hours. The resin was recovered by centrifugation (2,100 g, 5 min) and the supernatant containing the fusion proteins was subjected to buffer exchange to PBS and was simultaneously concentrated by ultrafiltration using a stirred-cell concentrator (Amicon, Beverly Mass.; model 8400). The purified fusion proteins were analyzed by Western blot analyses (FIG. 2).

Example 3

Biochemical Characterization of MBP::VP6 Fusion Protein

It has been shown that recombinant VP6 expressed by the bacculovirus expression system forms structures that resemble double-layered rotavirus particles when examined by electron microscopy. Purified MBP::VP6 fusion protein was analyzed by sucrose gradients to determine if these fusion proteins assembled into organized structures resembling virus particles that could be fractionated in a sucrose gradient. MBP::VP6 was subjected to centrifugation (SW 50, 35,000 g, 60 min) through a 4 ml sucrose gradient (20–50%) on a 1 ml cesium chloride cushion (60%). A total of 16, 300-$\mu$l fractions were collected. Distribution of MBP::VP6 in the sucrose gradient and cesium chloride cushion was analyzed by Western blot analysis and distribution of virus particles was analyzed by silver nitrate staining of the SDS-gel (FIG. 3). The results showed that MBP::VP6 remained in the top 4 fractions of the gradient, while double-layered virus particles devoid of VP4 and VP7 were recovered from fraction #11 to #12 of the sucrose gradient and in the cesium chloride cushion (fraction #16). The difference in the distribution behavior of MBP::VP6 in the gradient indicated that the fusion protein does not form virus-like structures.

Analysis of the Immune Response from Subjects Immunized with VP-6 Fusion Proteins Example 4

Method of Vaccination and Challenge

Six-week-old virus antibody free female BALB/c mice were purchased from Harlan Sprague-Dawley (Indianapolis, Ind.). Animals were housed four animals to a cage in sterile micro barrier cages. Between four and ten animals were included in each group. Animals were ear tagged and a blood and stool specimen was collected from each animal prior to vaccination.

Expressed fusion protein of EDIM VP6 or portions of VP6 were used as the immunizing antigens. Protein concentration was calculated to be 176 ng/$\mu$l. Animals received 50 $\mu$l of VP6 (8.8 $\mu$g) per dose. Animals received either two or three doses separated by two-week intervals. The adjuvant used was *E. coli* LT (R192G) at 1 mg/ml received from Dr. John Clements (Tulane University). The LT was resuspended in deionized $H_2O$ and 10 mM $CaCl_2$. Intranasal inoculations included 10 $\mu$g LT with antigen. Adjuvant and antigens were mixed prior to immunization. Animals were immunized intranasally (i.n.) by lightly anesthetizing with metofane and instilling approximately 5 $\mu$l per nostril until the entire dose was delivered.

Four weeks after the last immunization, animals were bled and a stool specimen was collected from each animal to measure antibody responses. Animals were challenged with 100 $\mu$l of a 1:25 fold dilution of EDIM P9 12/15/97 $1\times10^7$ ffu/ml to give a dose of $4\times10^4$ ffu or 100 $ID_{50}$ Stool specimens [two pellets in 0.5 ml of Earl's Balanced Salt Solution (EBSS)] were collected from each mouse for seven days and stored at −20° C. Rotavirus antigen was measured in the stools by EIA to determine shedding.

Twenty-one days after challenge, sera and stool specimens were obtained again to measure antibody responses.

Example 5

EIA Method to Measure Rotavirus Antigen in Stool to Determine Shedding

Stool specimens for Example 4 were thawed, homogenized and centrifuged (500 g, 10 min). For rotavirus antigen determination, 96-well EIA plates (Corning Costar Co., Corning, N.Y.) were coated overnight at 4° C. with 100 $\mu$l per well of either rabbit antibody to rotavirus (duplicate positive wells) or preimmune rabbit serum (duplicate negative wells). Plates were washed and 50 $\mu$l of stool supernatant was added to duplicate wells coated with each antibody. After one hour incubation at 37° C. on a rotation platform, plates were washed and 50 $\mu$l normal goat serum (Vector Laboratory, Inc., Burlingame, Calif.) diluted 100-fold in phosphate-buffered saline containing 5% nonfat dry milk (PBS-M) was added for 15 minutes at room temperature. Fifty microliters of guinea pig antibody to rotavirus diluted 1:500 in PBS-M containing a 1:50 dilution of normal rabbit serum (DAKO, Carpinteria, Calif.) was added and incubated for 30 minutes. Plates were washed and 50 $\mu$l of a 1:200 dilution of biotinylated goat anti-guinea pig IgG (Vector) in PBS-M containing a 1:50 dilution of normal rabbit serum was added and incubated 30 minutes. After washing plates, 50 $\mu$l of a 1:100 dilution of peroxidase-conjugated avidin-biotin (Vector) in wash buffer was added and incubated 30 minutes. The plates were washed and 50 $\mu$l substrate phenylenediamine with $H_2O_2$ in citric acid-phosphate buffer) was added and incubated (room temperature) for 15 minutes. The reaction was stopped with 75 $\mu$l of 1.0 M $H_2SO_4$. The absorbance at 490 nm was measured and the net optical densities were determined by subtracting the average of the negative wells from the average of the positive wells. The specimen was considered positive for rotavirus if the average absorbance of the positive wells was greater than or equal to two times that of the negative wells and greater than or equal to 0.15.

A time course of fecal shedding of rotavirus in mice challenged with EDIM is shown in FIG. 4. The open circles represent data points from EDIM challenged control mice exposed to a control vaccination containing the LT adjuvant but lacking the rotavirus fusion proteins of the present invention. The filled squares represent data points from EDIM challenged experimental mice that were intranasally vaccinated with the VP6::MBP rotavirus fusion vaccine composition of the present invention. As can be seen from the figure, the incidence of fecal shedding increased from the first day after EDIM challenge in the control mice until reaching a maximum value on the fourth day after challenge.

In contrast, mice vaccinated with the VP6::MBP rotavirus fusion protein vaccine composition produce little fecal shedding over the same period of time. These data clearly show that intranasal vaccination of mice with a VP6::MBP rotavirus fusion vaccine composition greatly reduced the incidence of fecal shedding of virus after rotavirus EDIM challenge. Correlating levels of fecal shedding to levels of infection, vaccination with the VP6::MBP rotavirus fusion vaccine composition of the present invention provides protection against EDIM challenge in mice.

Example 6

EIA Method to Measure Serum Rotavirus IgG and IgA and Stool Rotavirus IgA

Serum rotavirus IgA and IgG and rotavirus stool IgA were measured as follows. EIA plates (Corning Costar Co., Corning, N.Y.) were coated overnight at 4° C. with anti-rotavirus rabbit IgG. After washing with phosphate buffered saline plus 0.05% Tween 20, 50 μl of EDIM viral lysate or mock-infected cell lysate were each added to duplicate positive and duplicate negative wells and plates were incubated for one hour at 37° C. on a rotation platform. After washing plates, 50 μl of serial two-fold dilutions of pooled sera from EDIM infected mice assigned concentrations of 160,000 or 10,000 units/ml of rotavirus IgG or IgA, respectively, were added to duplicate wells coated with either EDIM-infected or uninfected MA104 cell lysates to generate a standard curve. Serial 10-fold dilutions of mouse sera to be tested were also added to duplicate wells of each lysate and incubated 1 hour. This was followed by sequential addition of biotin-conjugated goat anti-mouse IgG or IgA (Sigma Chemical Co., St. Louis, Mo.), peroxidase-conjugated avidin-biotin (Vector Laboratories), and o-phenylenediamine substrate (Sigma Chemical Co.). Color development was stopped after fifteen minutes with 1 M $H_2SO_4$ and the $A_{490}$ was measured. Titers of rotavirus IgG or IgA, expressed as units/ml, were determined from the standard curve generated by subtraction of the average $A_{490}$ values of the duplicate cell lysate wells from the average of the wells coated with EDIM lysate.

For determination of stool rotavirus IgA, two stool pellets were collected into 0.5 ml of EBSS, homogenized, and centrifuged (1,500 g, 5 min). Stool rotavirus IgA was then measured by the method described above.

The data from these experiments showed that mice immunized with the recombinant MBP::VP6 rotavirus fusion protein vaccines generated an immune response directed against the VP6 fusion protein. Both serum IgG and IgA responses were noted. The serum IgG responses were higher than those of the IgA responses. Concerning the IgG responses, administration of the recombinant rotavirus protein intramuscularly with the adjuvant QS-21 appeared to produce a greater IgG response than when the protein was administered intranasally in combination with the adjuvant LT. In contrast, intranasal administration with LT as the adjuvant produced a greater serum IgA response. Stool IgA was also greater when vaccination was performed intranasally using LT as the adjuvant.

Example 7

EIA Method to Measure Rotavirus Antizen in Stool to Determine Shedding

Stool specimens were thawed, homogenized and centrifuged (500 g, 10 min). For rotavirus antigen determination, 96-well EIA plates (Corning Costar Co.) were coated overnight at 4° C. with 100 μl/well of either rabbit antibody to rotavirus (duplicate positive wells) or preimmune rabbit serum (duplicate negative wells). Plates were washed and 50 μl of stool supernatant or serial two-fold dilutions of purified preparation of double-layered EDIM particles (standard) was added to duplicate wells coated with each antibody. After incubation at 37° C. for one hour on a rotation platform, plates were washed and 50 μl normal goat serum (Vector) diluted 100-fold in phosphate-buffered saline containing 50% nonfat dry milk (PBS-M) was added for 15 minutes at room temperature. Fifty microliters of guinea pig antibody to rotavirus diluted 1:500 in PBS-M containing a 1:50 dilution of normal rabbit serum (DAKO) was added and incubated for 30 minutes. Plates were washed and 50 μl of a 1:200 dilution of biotinylated goat anti-guinea pig IgG (Vector) in PBS-M containing a 1:50 dilution of normal rabbit serum was added and incubated 30 minutes. After washing plates, 50 μl of a 1:100 dilution of peroxidase-conjugated avidin-biotin (Vector) in wash buffer was added and incubated 30 minutes. The plates were washed and 50 μl substrate (o-phenylenediamine with $H_2O_2$ in citric acid-phosphate buffer) was added and incubated (room temperature) for 15 minutes. The reaction was stopped with 75 μl of 1.0 M $H_2SO_4$. The absorbance at 490 nm was measured and the net optical densities were determined by subtracting the average of the negative wells from the average of the positive wells. Values obtained from a standard curve generated from the serially diluted double-layered particles were used to determine concentrations of rotavirus protein in each specimen. The limit of detection was 3 ng/ml.

Reduction of shed rotavirus antigen was 79, 92 and almost 100% for MHP::$VP6_{AB}$, MBP::$VP6_{BC}$ and MBP::$VP6_{CD}$, respectively (Table 1). Therefore, the region CD was sufficient to elicit the same level of protection as the entire VP6 protein. It should be noted that MBP::$VP6_{BC}$ also provided excellent protection.

TABLE 1

Rotavirus antigen (ng/ml) shed in BALB/c mice immunized with MBP::VP6, MPB::$VP6_{AB}$, MBP::$VP6_{BC}$ or MBP::$VP6_{CD}$

| Vaccine | Mouse Number | Day 1 | 2 | 3 | 4 | 5 | 6 | 7 | Mean shedding per mouse per day | Reduction in shedding relative to control |
|---|---|---|---|---|---|---|---|---|---|---|
| None | 1 | 0 | 25 | 122 | 131 | 88 | 395 | 13 | 42.66 | |
| | 2 | 0 | 0 | 0 | 0 | 0 | 0 | 0 | | |
| | 3 | 0 | 0 | 48 | 569 | 49 | 7 | 23 | | |
| | 4 | 0 | 0 | 14 | 22 | 23 | 25 | 0 | | |
| | 5 | 0 | 0 | 19 | 60 | 222 | 23 | 20 | | |
| | 6 | 0 | 0 | 19 | 85 | 19 | 9 | 0 | | |

TABLE 1-continued Rotavirus antigen (ng/ml) shed in BALB/c mice immunized with MBP::VP6, MPB::VP6$_{AB}$, MBP::VP6$_{BC}$ or MBP::VP6$_{CD}$

| Vaccine | Mouse Number | Day 1 | 2 | 3 | 4 | 5 | 6 | 7 | Mean shedding per mouse per day | Reduction in shedding relative to control |
|---|---|---|---|---|---|---|---|---|---|---|
|  | 7 | 0 | 0 | 25 | 161 | 25 | 8 | 7 |  |  |
|  | 8 | 0 | 0 | 17 | 58 | 28 | 24 | 6 |  |  |
| MBP::VP6 | 1 | 0 | 0 | 0 | 0 | 0 | 0 | 0 | 0.96 | 97.75% |
|  | 2 | 0 | 19 | 0 | 0 | 0 | 0 | 0 |  |  |
|  | 3 | 0 | 0 | 0 | 0 | 0 | 0 | 0 |  |  |
|  | 4 | 0 | 0 | 12 | 0 | 0 | 0 | 0 |  |  |
|  | 5 | 0 | 15 | 0 | 0 | 0 | 0 | 0 |  |  |
|  | 6 | 0 | 8 | 0 | 0 | 0 | 0 | 0 |  |  |
|  | 7 | 0 | 0 | 0 | 0 | 0 | 0 | 0 |  |  |
|  | 8 | 0 | 0 | 0 | 0 | 0 | 0 | 0 |  |  |
| MBP::VP6$_{AB}$ | 1 | 0 | 29 | 30 | 9 | 8 | 0 | 0 | 8.76 | 79.47% |
|  | 3 | 0 | 10 | 43 | 10 | 0 | 0 | 0 |  |  |
|  | 4 | 0 | 14 | 26 | 0 | 0 | 0 | 0 |  |  |
|  | 5 | 0 | 7 | 11 | 17 | 10 | 14 | 0 |  |  |
|  | 6 | 0 | 0 | 81 | 15 | 7 | 8 | 0 |  |  |
|  | 7 | 0 | 0 | 5 | 16 | 11 | 16 | 0 |  |  |
|  | 8 | 0 | 12 | 20 | 0 | 0 | 0 | 0 |  |  |
| MBP::VP6$_{BC}$ | 1 | 0 | 0 | 0 | 0 | 0 | 0 | 0 | 3.23 | 92.43% |
|  | 2 | 0 | 0 | 0 | 0 | 0 | 0 | 0 |  |  |
|  | 3 | 0 | 0 | 0 | 0 | 6 | 17 | 0 |  |  |
|  | 4 | 0 | 0 | 6 | 0 | 0 | 0 | 0 |  |  |
|  | 5 | 0 | 9 | 4 | 13 | 9 | 28 | 11 |  |  |
|  | 6 | 0 | 0 | 4 | 11 | 0 | 9 | 0 |  |  |
|  | 7 | 0 | 0 | 19 | 6 | 0 | 21 | 0 |  |  |
|  | 8 | 0 | 0 | 0 | 0 | 8 | 0 | 0 |  |  |
| MBP::VP6$_{CD}$ | 1 | 0 | 0 | 0 | 0 | 0 | 0 | 0 | 0.13 | 99.70% |
|  | 2 | 0 | 0 | 0 | 0 | 0 | 0 | 0 |  |  |
|  | 3 | 0 | 0 | 0 | 0 | 0 | 0 | 0 |  |  |
|  | 4 | 0 | 0 | 0 | 0 | 0 | 0 | 0 |  |  |
|  | 5 | 0 | 0 | 0 | 0 | 0 | 0 | 0 |  |  |
|  | 6 | 0 | 0 | 0 | 0 | 0 | 0 | 0 |  |  |
|  | 7 | 0 | 0 | 0 | 0 | 0 | 0 | 0 |  |  |
|  | 8 | 0 | 7 | 0 | 0 | 0 | 0 | 0 |  |  |

A value of 0 indicates that shedding was below the limit of detection, i.e., <3 ng/ml

Example 8

Comparison of the Adjuvants LT and CT

*E. coli* LT toxin was shown to be a very efficient adjuvant in inducing protection when inoculation intranasally with the rotavirus subunit vaccine MBP::VP6. (See Example 4, 5, and 6). The effectiveness of *V. cholerae* toxin (CT) as an intranasal adjuvant was compared with LT. Mice were immunized with three doses of MBP::VP6 together with either 10 μg of CT or LT. Shedding data following virus challenge indicated that shedding was reduced by 98% irrespective of whether CT or LT was used (Table 2). Measurement of VP6-specific antibodies (Table 3) revealed that specific IgG antibodies were induced by MBP::VP6 when co-administered with CT (GMT)=158,115 U/ml) or LT (GMT=417,604 U/ml). Specific serum IgA was induced in CT-MT=431 U/ml) and LT-(GMT=1,185 U/ml) inoculated mice. Low but detectable stool IgA titers were also induced by CT (GMT=41 U/ml) as was as LT (GMT=77 U/ml). Therefore, both adjuvants could induce VP6 specific serum and mucosal antibodies.

TABLE 2

Rotavirus antigen shed (ng/ml) in BALB/c mice immunized with 3 doses of MBP::VP6 with *E. coli* LT or *V. cholerae* CT adjuvant

| Adjuvant | Mouse Number | Day 1 | 2 | 3 | 4 | 5 | 6 | 7 | Mean shedding per mouse per day | Reduction in shedding relative to control |
|---|---|---|---|---|---|---|---|---|---|---|
| None | 1 | 0 | 25 | 122 | 131 | 88 | 395 | 13 | 42.66 |  |
|  | 2 | 0 | 0 | 0 | 0 | 0 | 0 | 0 |  |  |
|  | 3 | 0 | 0 | 48 | 569 | 49 | 7 | 23 |  |  |
|  | 4 | 0 | 0 | 14 | 22 | 23 | 25 | 0 |  |  |
|  | 5 | 0 | 0 | 19 | 60 | 222 | 23 | 20 |  |  |

TABLE 2-continued

Rotavirus antigen shed (ng/ml) in BALB/c mice immunized with 3 doses of MBP::VP6 with *E. coli* LT or *V. cholerae* CT adjuvant

| Adjuvant | Mouse Number | \multicolumn{7}{c}{Day} | Mean shedding per mouse per day | Reduction in shedding relative to control |
|---|---|---|---|---|---|---|---|---|---|---|

| Adjuvant | Mouse Number | 1 | 2 | 3 | 4 | 5 | 6 | 7 | Mean shedding per mouse per day | Reduction in shedding relative to control |
|---|---|---|---|---|---|---|---|---|---|---|
| | 6 | 0 | 0 | 19 | 85 | 19 | 9 | 0 | | |
| | 7 | 0 | 0 | 25 | 161 | 25 | 8 | 7 | | |
| | 8 | 0 | 0 | 17 | 58 | 28 | 24 | 6 | | |
| LT | 1 | 0 | 0 | 0 | 0 | 0 | 0 | 0 | 0.96 | 97.75% |
| | 2 | 0 | 19 | 0 | 0 | 0 | 0 | 0 | | |
| | 3 | 0 | 0 | 0 | 0 | 0 | 0 | 0 | | |
| | 4 | 0 | 0 | 12 | 0 | 0 | 0 | 0 | | |
| | 5 | 0 | 15 | 0 | 0 | 0 | 0 | 0 | | |
| | 6 | 0 | 8 | 0 | 0 | 0 | 0 | 0 | | |
| | 7 | 0 | 0 | 0 | 0 | 0 | 0 | 0 | | |
| | 8 | 0 | 0 | 0 | 0 | 0 | 0 | 0 | | |
| CT | 1 | 0 | 0 | 0 | 0 | 0 | 0 | 0 | 0.71 | 98.34% |
| | 2 | 0 | 0 | 0 | 0 | 0 | 0 | 0 | | |
| | 3 | 0 | 0 | 0 | 0 | 0 | 0 | | | |
| | 4 | 0 | 0 | 0 | 0 | 0 | 0 | 0 | | |
| | 5 | 0 | 0 | 0 | 0 | 0 | 0 | 0 | | |
| | 6 | 0 | 0 | 0 | 0 | 0 | 0 | 0 | | |
| | 7 | 0 | 0 | 0 | 0 | 0 | 0 | 0 | | |
| | 8 | 0 | 18 | 0 | 0 | 13 | 0 | 0 | | |

A value of 0 indicates that shedding was below the limit of detection, i.e., 3 ng/ml

TABLE 3

Rotavirus-specific antibodies (U/ml) in sera collected from BALB/c mice immunized with MBP::VP6 and with either LT or CT

| Adjuvant | Mouse Number | Serum IgG | | | Serum IgA | | | Stool IgA | | |
|---|---|---|---|---|---|---|---|---|---|---|
| | | Pre-vaccination | Pre-challenge | Post-challenge | Pre-vaccination | Pre-challenge | Post-challenge | Pre-vaccination | Pre-challenge | Post-challenge |
| None | 1 | <100 | <100 | 9,710 | <100 | <100 | 7,284 | <5 | 17 | 4,517 |
| | 2 | <100 | <100 | <100 | <100 | <100 | <100 | <5 | 12 | 10 |
| | 3 | <100 | <100 | 5,674 | <100 | <100 | 8,790 | <5 | 13 | 5,920 |
| | 4 | <100 | <100 | 6,324 | <100 | <100 | 4,885 | <5 | <5 | 1,986 |
| | 5 | <100 | <100 | 4,233 | <100 | <100 | 9,677 | <5 | 16 | 2,325 |
| | 6 | <100 | <100 | 1,545 | <100 | <100 | 2,511 | <5 | 20 | 4,513 |
| | 7 | <100 | <100 | 4,596 | <100 | <100 | 8,117 | <5 | 8 | 3,576 |
| | 8 | <100 | <100 | 6,216 | <100 | <100 | 2,567 | <5 | 13 | 1,541 |
| | GMT | | | 2,997 | | | 5,531 | | 12 | 1,534 |
| LT | 1 | <100 | 378,240 | 1,292,000 | <100 | 995 | 32,544 | <5 | 73 | 7,732 |
| | 2 | <100 | 311,525 | 1,627,000 | <100 | 2,401 | 3,327 | <5 | 57 | 4,717 |
| | 3 | <100 | 297,683 | 1,187,000 | <100 | 560 | 35,774 | <5 | 22 | 10,082 |
| | 4 | <100 | 273,683 | 1,072,00 | <100 | 720 | 17,524 | <5 | 30 | 4,550 |
| | 5 | <100 | 599,120 | 1,203,000 | <100 | 816 | 36,883 | <5 | 40 | 8,829 |
| | 6 | <100 | 481,863 | 498,618 | <100 | 1,373 | 14,169 | <5 | 658 | 4,690 |
| | 7 | <100 | 359,574 | 1,742,000 | <100 | 1,035 | 5,980 | <5 | 189 | 7,972 |
| | 8 | <100 | 929,583 | 1,195,000 | <100 | 3,486 | 28,791 | <5 | 90 | 5,771 |
| | GMT | | 417,604 | 1,162,701 | | 1,185 | 16,720 | | 77 | 6,500 |
| CT | 1 | <100 | 226,207 | 1,623,000 | <100 | 561 | 4,863 | <5 | 32 | 3,717 |
| | 2 | <100 | 213,608 | 342,506 | <100 | 1,314 | 10,501 | <5 | 83 | 5,260 |
| | 3 | <100 | 202,023 | 2,416,000 | <100 | 496 | 4,178 | <5 | 78 | 2,832 |
| | 4 | <100 | 178,661 | 475,848 | <100 | 366 | 21,325 | <5 | 67 | 5,431 |
| | 5 | <100 | 69,919 | 1,233,000 | <100 | 112 | 4,634 | <5 | 34 | 4,356 |
| | 6 | <100 | 225,320 | 507,162 | <100 | 946 | 24,361 | <5 | 41 | 4,953 |
| | 7 | <100 | 220,965 | 3,612,000 | <100 | 209 | 6,575 | <5 | 29 | 17,237 |
| | 8 | <100 | 64,345 | 402,845 | <100 | 402 | 42,188 | <5 | 14 | 9,515 |
| | GMT | | 158,115 | 934,476 | | 431 | 10,452 | | 41 | 5,667 |

Titers of <100 U/ml indicate that no serum rotavirus IgG or IgA was detected.
Titers of <5 U/ml indicate that no stool IgA was detected.
GMT = geometric mean titer

Example 9

Optimization of the Immunization Protocol Determination of the Number of Doses to Elicit a Protective Immunity

As seen in the previous examples, 2 or 3 doses of the MBP::VP6 induced almost complete protection. To determine if 1 or 2 doses could provide the same level of protection, mice were immunized intranasally with 1, 2 or 3 doses of MBP::VP6 (8.8 µg/dose) using LT as adjuvant. For the latter two groups, doses were given at 14 days apart. Measurement of serum rotavirus-specific IgG indicated that the levels of IgG induced by three doses (GMT=417,604 U/ml) was higher than two doses (GMT=122,839 U/ml), which in turn was higher than one dose (GMT=32,843 U/ml; Table 4). Serum IgA titers for 3 doses were higher (GMA= 1,185 U/ml) than 2 doses (GMT=256 U/ml) or 1 dose (GMT=243 U/ml). Larger titers of stool IgA could be detected in mice receiving 3 doses (GMT=77 U/ml) than 2 doses (GMT=24 U/ml). Only a few animals receiving 1 dose developed measurable stool rotavirus IgA (GMT=12 U/ml).

Although the immunological responses differed between the 1, 2 and 3 dose protocols, animals were shown to be protected by a single vaccination. Analyses of the quantities of rotavirus antigen shed following rotavirus challenge one month after the last or only immunization indicated that 1, 2 or 3 doses of the vaccine resulted in almost 100, 98 and 98% reduction in shedding, respectively (Table 5). Therefore, one dose of MBP::VP6 was sufficient to induce essentially complete protection and protection appeared to be independent of the titer of specific antibodies.

TABLE 4

Rotavirus-specific antibodies in sera collected from mice immunized with 1, 2, or 3 doses of MBP::VP6

| Adjuvant | Mouse Number | Serum IgG Pre-vaccination | Serum IgG Pre-challenge | Serum IgG Post-challenge | Serum IgA Pre-vaccination | Serum IgA Pre-challenge | Serum IgA Post-challenge | Pre-vaccination | Stool IgA Pre-challenge | Stool IgA Post-challenge |
|---|---|---|---|---|---|---|---|---|---|---|
| None | 1 | <100 | <100 | 9,710 | <100 | <100 | 7,284 | <5 | 17 | 4,517 |
|  | 2 | <100 | <100 | <100 | <100 | <100 | <100 | <5 | 12 | 10 |
|  | 3 | <100 | <100 | 5,674 | <100 | <100 | 8,790 | <5 | 13 | 5,920 |
|  | 4 | <100 | <100 | 6,324 | <100 | <100 | 4,885 | <5 | <5 | 1,986 |
|  | 5 | <100 | <100 | 4,233 | <100 | <100 | 9,677 | <5 | 16 | 2,325 |
|  | 6 | <100 | <100 | 1,545 | <100 | <100 | 2,511 | <5 | 20 | 4,513 |
|  | 7 | <100 | <100 | 4,596 | <100 | <100 | 8,117 | <5 | 8 | 3,576 |
|  | 8 | <100 | <100 | 6,216 | <100 | <100 | 2,567 | <5 | 13 | 1,541 |
|  | GMT |  |  | 2,997 |  |  | 5,531 |  | 12 | 1,534 |
| 1 dose | 1 | <100 | 64,219 | 804,286 | <100 | 468 | 90,536 | <5 | 39 | 10,982 |
|  | 3 | <100 | 19,511 | 836,468 | <100 | 682 | 23,666 | <5 | 10 | 7,445 |
|  | 3 | <100 | 29,575 | 53,079 | <100 | 188 | 415 | <5 | 27 | 33 |
|  | 5 | <100 | 43,111 | 446,253 | <100 | 391 | 22,207 | <5 | 11 | 9,649 |
|  | 6 | <100 | 30,789 | 442,076 | <100 | 166 | 20,193 | <5 | 6 | 5,108 |
|  | 7 | <100 | 46,633 | 638,240 | <100 | 129 | 23,968 | <5 | 9 | 9,638 |
|  | 8 | <100 | 17,970 | 908,344 | <100 | <100 | 37,835 | <5 | 6 | 7,318 |
|  | GMT |  | 32,843 | 455,751 |  | 243 | 16,696 |  | 12 | 3,694 |
| 2 doses | 1 | <100 | 80,175 | 890,661 | <100 | <100 | 29,583 | <5 | 18 | 7,633 |
|  | 2 | <100 | 80,966 | 731,137 | <100 | 223 | 80,418 | <5 | 13 | 7,096 |
|  | 3 | <100 | 137,609 | 628,817 | <100 | 406 | 39,014 | <5 | 76 | 6,886 |
|  | 4 | <100 | 194,994 | 1,887,000 | <100 | 578 | 98,965 | <5 | 93 | 13,548 |
|  | 5 | <100 | 131,460 | 930,027 | <100 | 329 | 45,098 | <5 | 8 | 2,973 |
|  | 6 | <100 | 164,938 | 865,635 | <100 | 131 | 43,500 | <5 | 16 | 6,599 |
|  | 7 | <100 | 103,431 | 836,212 | <100 | 180 | 228,623 | <5 | 15 | 9,840 |
|  | 8 | <100 | 132,712 | 1,148,000 | <100 | 456 | 68,520 | <5 | 35 | 10,097 |
|  | GMT |  | 122,839 | 937,588 |  | 256 | 64,023 |  | 24 | 7,485 |
| 3 doses | 1 | <100 | 378,240 | 1,292,000 | <100 | 995 | 32,544 | <5 | 73 | 7,732 |
|  | 2 | <100 | 311,525 | 1,627,000 | <100 | 2,401 | 3,327 | <5 | 57 | 4,717 |
|  | 3 | <100 | 297,229 | 1,187,000 | <100 | 560 | 35,774 | <5 | 22 | 10,082 |
|  | 4 | <100 | 273,683 | 1,072,000 | <100 | 720 | 17,524 | <5 | 30 | 4,550 |
|  | 5 | <100 | 599,120 | 1,203,000 | <100 | 815 | 36,883 | <5 | 40 | 8,829 |
|  | 6 | <100 | 481,863 | 498,618 | <100 | 1,373 | 14,169 | <5 | 658 | 4,690 |
|  | 7 | <100 | 359,574 | 1,742,000 | <100 | 1,035 | 5,980 | <5 | 189 | 7,972 |
|  | 8 | <100 | 929,583 | 1,195,000 | <100 | 3,486 | 28,791 | <5 | 90 | 5,771 |
|  | GMT |  | 417,604 | 1,162,701 |  | 1,185 | 16,720 |  | 77 | 6,500 |

Titers of <100 U/ml indicate that no serum rotavirus IgG or IgA was detected.
Titers of <5 U/ml indicate that no stool IgA was detected
GMT = geometric mean titer

TABLE 5

Rotavirus antigen (ng/ml) shed in BALB/c mice immunized with EDIM after immunization with 1, 2 or 3 doses of MBP::VP

| Number of Doses | Mouse Number | Day 1 | 2 | 3 | 4 | 5 | 6 | 7 | Mean shedding per mouse per day | Reduction in shedding relative to control |
|---|---|---|---|---|---|---|---|---|---|---|
| None | 1 | 0 | 25 | 122 | 131 | 88 | 395 | 13 | 42.66 | |
| | 2 | 0 | 0 | 0 | 0 | 0 | 0 | 0 | | |
| | 3 | 0 | 0 | 48 | 569 | 49 | 7 | 23 | | |
| | 4 | 0 | 0 | 14 | 22 | 23 | 25 | 0 | | |
| | 5 | 0 | 0 | 19 | 60 | 222 | 23 | 20 | | |
| | 6 | 0 | 0 | 19 | 85 | 19 | 9 | 0 | | |
| | 7 | 0 | 0 | 25 | 161 | 25 | 8 | 7 | | |
| | 8 | 0 | 0 | 17 | 58 | 28 | 24 | 6 | | |
| One dose | 1 | 0 | 0 | 0 | 0 | 0 | 0 | 0 | 0.20 | 99.53% |
| | 2 | 0 | 0 | 10 | 0 | 0 | 0 | 0 | | |
| | 3 | 0 | 0 | 0 | 0 | 0 | 0 | 0 | | |
| | 4 | 0 | 0 | 0 | 0 | 0 | 0 | 0 | | |
| | 5 | 0 | 0 | 0 | 0 | 0 | 0 | 0 | | |
| | 6 | 0 | 0 | 0 | 0 | 0 | 0 | 0 | | |
| | 7 | 0 | 0 | 0 | 0 | 0 | 0 | 0 | | |
| | 8 | 0 | 0 | 0 | 0 | 0 | 0 | 0 | | |
| Two doses | 1 | 0 | 25 | 0 | 0 | 0 | 0 | 0 | 1.02 | 97.61% |
| | 2 | 0 | 0 | 0 | 12 | 12 | 0 | 0 | | |
| | 3 | 0 | 0 | 0 | 0 | 0 | 0 | | | |
| | 4 | 0 | 0 | 0 | 0 | 0 | 0 | 0 | | |
| | 5 | 0 | 0 | 0 | 0 | 0 | 0 | 0 | | |
| | 6 | 0 | 8 | 0 | 0 | 0 | 0 | 0 | | |
| | 7 | 0 | 0 | 0 | 0 | 0 | 0 | 0 | | |
| | 8 | 0 | 0 | 0 | 0 | 0 | 0 | 0 | | |
| Three doses | 1 | 0 | 0 | 0 | 0 | 0 | 0 | 0 | 0.96 | 97.75% |
| | 2 | 0 | 19 | 0 | 0 | 0 | 0 | 0 | | |
| | 3 | 0 | 0 | 0 | 0 | 0 | 0 | 0 | | |
| | 4 | 0 | 0 | 12 | 0 | 0 | 0 | 0 | | |
| | 5 | 0 | 15 | 0 | 0 | 0 | 0 | 0 | | |
| | 6 | 0 | 8 | 0 | 0 | 0 | 0 | 0 | | |
| | 7 | 0 | 0 | 0 | 0 | 0 | 0 | 0 | | |
| | 8 | 0 | 0 | 0 | 0 | 0 | 0 | 0 | | |

A value of 0 indicates that shedding was below the limit of detection, i.e. <3 ng/ml)

Development of a Subunit Vaccine

To further facilitate the development of a safe and effective rotavirus vaccine candidate, the following work was performed to generate rotavirus fusion proteins containing an immunologically active fragment of VP6 for use as a vaccine candidate. Subunit vaccines are thought to be generally safer than killed virus or live-attenuated virus vaccines since only a portion of the virus is used to induce an immune response in a subunit vaccine, as opposed to the entire virus in either of the alternative methods. While use of entire viral proteins represents an advancement over whole virus vaccines, this approach could also be improved using partial protein or subunit vaccines. Such vaccines would reduce the cost of preparation and decrease the difficulties in preparing the needed quantities of viral protein to be used in the vaccine preparations. In light of this fact, the development of a bacteria-expressed subunit vaccine composed of a subset of those viral protein amino acids derivitized from these subunit vaccines that induce an immune response from an immunized individual would be advantageous. Accordingly, the examples below illustrate the methods used to generate a rotavirus fusion protein containing a subset of viral protein amino acids required to elicit an immune response from a vaccinated individual fused to a suitable fusion protein partner.

Example 10

Construction, Expression and Purification of Truncated VP6 Fusion Proteins

To produce a minimal subunit vaccine while retaining the original protective efficacy, three plasmids, pMAL-c2/EDIM6$_{AB}$, pMAL-c2/EDIM6$_{BC}$ and pMAL-c2/EDIM6$_{CD}$, were constructed to express truncated forms of VP6, wherein the truncated forms of VP6 contain immunogenic fragments of a rotavirus protein. Recombinant plasmids pMAL-c2/EDIM6$_{AB}$, pMAL-c2/EDIM6$_{BC}$ and pMAL-c2/EDIM6$_{CD}$, containing truncated forms of VP6 were constructed using the same strategy that was used for the construction of pMAL-c2/EDIM6, as seen in Example 1. These plasmids expressed MBP::VP6$_{AB}$ containing amino acids 1 to 196, MBP::VP6$_{BC}$ containing amino acid 97 to 297 and MBP::VP6$_{CD}$ containing amino acids 197 to 397. (See FIG. 5). To construct these plasmids, cDNAs were synthesized by polymerase chain reaction (PCR) using pMAL-c2/EDIM6 (see Example 1) as the template. The gene specific primers used for construction and the regions of VP6 cloned are summarized in Table 6.

TABLE 6

Primers used to clone pMAL-c2/MBP$_{AB}$, pMAL-c2/EDIM6$_{BC}$ and pMAL-c2/EDIM6$_{CD}$

| Plasmid | Name of Fusion Protein | Primers |
|---|---|---|
| pMAL-c2/MBP$_{AB}$ | MBP::VP6$_{AB}$ | Forward primer: atg gat gtg ctg tac tct atc SEQ ID NO. 1 |
| | | Reverse primer: tca cga gta gtc gaa tcc tgc aac SEQ ID NO. 2 |
| pMAL-c2/EDIM6$_{BC}$ | MBP::VP6$_{BC}$ | Forward primer: atg gat gaa atg atg cga gag tca SEQ ID NO. 3 |
| | | Reverse primer: tca gaa tgg cgg tct cat caa ttg SEQ ID NO. 4 |
| pMAL-c2/EDIM6$_{CD}$ | MBP::VP6$_{CD}$ | Forward primer: tgc gca att aat gct cca gct SEQ ID NO. 5 |
| | | Reverse primer: tca ctt tac cag cat gct tct aat SEQ ID NO. 6 |

Once constructed, the plasmids encoding the truncated VP6 fragments were introduced into bacteria for protein expression. Recombinant bacteria containing pMAL-c2/EDIM6$_{AB}$, PMAL-c2/EDIM6$_{BC}$ and PMAL-c2/EDIM6$_{CD}$ were grown as described in the examples above. Specifically, an overnight culture was grown (37° C.; shaken at 215 rpm) in rich broth (tryptone, 10 gm; yeast extract, 5 gm; NaCl, 5 gm; glucose, 2 gm; and ampicillin, 100 mg per liter). On the following day, 10 ml of overnight culture for each vector were inoculated into 1 liter of rich broth. The culture was grown until the optical density reached ~0.6 OD$_{600}$. IPTG was added (0.3 mM) to induce expression of fusion protein. Growth was continued for 3 hours.

As previously described for MBP::VP6, cells expressing MBP::VP6$_{AB}$, MBP::VP6$_{BC}$ or MBP::VP6$_{DC}$ were harvested by centrifugation (4,000 g; 20 minutes). The cells were washed in PBS and then recovered by centrifugation. The cell pellet was frozen at −20° C., thawed slowly in cold water, and resuspended in a total of 50 ml of buffer L (5 mM NaH$_2$PO$_4$, 10 mM Na$_2$HPO$_4$, 30 mM NaCl, 10 mM β-mercaptoethanol, 0.2% Tween 20, 1 mM PMSF, 25 mM benzamidine, and 200 μg/ml of lysozyme). After digestion for 15 minutes (room temperature), the suspension was sonicated by three 30 second bursts (BioSonic IV, 50% power setting) while placed in an ice/water bath. NaCl (265 mg) and RNase A (5 μl of 10 mg/ml) were added to each 10 ml of sonicated cell lysate. The lysate was then centrifuged (54,000 g, 30 minutes) to obtain a supernatant containing a crude preparation of fusion protein. Fusion proteins in the various crude preparation were purified by affinity chromatography as described for MBP::VP6. The individual supernatants containing the various fusion protein constructs were mixed with amylose resin (New England Biolabs, Beverly Mass.) for 2 hours in a 500-ml flask on a rocker. After centrifugation (2,100 g, 5 minutes), the resin was recovered, then resuspended in 50 ml of buffer C (Buffer L containing 0.5 M NaCl), rocked for 30 minutes and finally centrifuged to recover the resin. The resin was washed in this manner 3 times and then washed overnight with 500 ml of buffer C. On the following day, the resin was recovered by centrifugation and resuspended in 50 ml of buffer D (50 mM Tris-HCl, pH 7.5; 50 mM NaCl; 1 mM EDTA; 10 mM β-mercaptoethanol; 1 mM PMSF), and rocked for 30 minutes. The resin was spun down and the bound fusion protein was eluted from the resin by suspending the resin in 250 ml of 15 mM maltose in buffer D for 2 hours. The resin was recovered by centrifugation and the supernatant containing the fusion proteins was subjected to buffer exchange to PBS and was simultaneously concentrated by ultrafiltration using a stirred-cell concentrator (Amicon, Beverly Mass.; model 8400).

Example 11

Vaccination and Challenge of Mice Using Truncated VP6 Fusion Proteins

Six-week-old immunologically naive female BALB/c mice (Harlan Sprague) and B cell deficient μMt mice were used to study the ability of the various truncated VP6 fusion proteins to elicit a protective response from vaccinated mice. Blood and stool specimens were collected from the animals prior to vaccination. Animals were immunized intranasally with 8.8 μg of fusion protein vaccines (MBP::VP6, MBP::VP6$_{AB}$, MBP::VP6$_{BC}$ or MBP::VP6$_{CD}$) in a 50-μl volume. Animals, which received three doses, were immunized at biweekly intervals. Animals received 10 μg of the adjuvant LT with the vaccines. E. coli LT(R192G) was supplied by Dr. John Clements of Tulane University.

Four weeks after the last immunization, animals were bled and stool specimens were collected to measure antibody responses. Each animal was challenged with a 100-ID$_{50}$ dose, which is equivalent to 4×10$^4$ ffu, of EDIM virus (Lot number: P9 12/15/97). Two stool pellets were collected in 0.5 ml of Earl's Balanced Salt Solution (EBSS) from each mouse for seven days and stored at −20° C. Rotavirus antigen was measured in the stools by EIA to determine shedding. Twenty one days after challenge, sera and stool specimens were obtained again to measure antibody responses.

Example 12

Measurement of Serum Rotavirus IgG and IgA and Stool Rotavirus IgA

Serum rotavirus IgA and IgG and rotavirus stool IgA were measured by EIA. EIA plates (Corning Costar Co.) were coated overnight at 4° C. with anti-rotavirus rabbit IgG. After washing with phosphate buffered saline plus 0.05% Tween 20, 50 μl of EDIM viral lysate or mock-infected cell lysate were each added to duplicate positive and duplicate negative wells for one hour at 37° C. on a rotation platform. After washing plates, 50 μl of serial two-fold dilutions of pooled sera from EDIM infected mice assigned concentrations of 160,000 or 10,000 units/ml of rotavirus IgG or IgA, respectively, were added to duplicate wells coated with either EDIM-infected or uninfected MA104 cell lysates to generate a standard curve. Serial 10-fold dilutions of mouse sera to be tested were also added to duplicate wells of each lysate and incubated for 1 hour. This was followed by sequential addition of biotin-conjugated goat anti-mouse IgG or IgA (Sigma Chemical Co.), peroxidase-conjugated fragment induced specific stool IgA (GMT=70 U/ml) which was similar to the titer induced by the entire VP6 (GMT=77 U/ml, Table 3). Fragment AB induced marginally detectable titers while (GMT=20 U/ml) BC did not induce any stool IgA. Therefore, the protection generated with inoculation of BC appeared to be unrelated to stool rotavirus IgA.

TABLE 7

Rotavirus-specific antibodies in sera collected from BALB/c mice immunized with MBP:PVP6$_{AB}$, MBP::VP6$_{BC}$ and MBP::VP6$_{CD}$ and LT

| Adju-vant | Mouse number | Serum IgG | | | Serum IgA | | | Stool IgA | | |
|---|---|---|---|---|---|---|---|---|---|---|
| | | Pre-vaccination | Pre-challenge | Post-challenge | Pre-vaccination | Pre-challenge | Post-challenge | Pre-vaccination | Pre-challenge | Post-challenge |
| None | 1 | <100 | <100 | 9,710 | <100 | <100 | 7,284 | <5 | 17 | 4,517 |
| | 2 | <100 | <100 | <100 | <100 | <100 | <100 | <5 | 12 | 10 |
| | 3 | <100 | <100 | 5,674 | <100 | <100 | 8,790 | <5 | 13 | 5,920 |
| | 4 | <100 | <100 | 6,324 | <100 | <100 | 4,885 | <5 | <5 | 1,986 |
| | 5 | <100 | <100 | 4,233 | <100 | <100 | 9,677 | <5 | 16 | 2,325 |
| | 6 | <100 | <100 | 1,545 | <100 | <100 | 2,511 | <5 | 20 | 4,513 |
| | 7 | <100 | <100 | 4,596 | <100 | <100 | 8,117 | <5 | 8 | 3,576 |
| | 8 | <100 | <100 | 6,216 | <100 | <100 | 2,567 | <5 | 13 | 1,541 |
| | GMT | | | 2,997 | | | 5,531 | | 12 | 1,534 |
| MBP::VP6$_{AB}$ | 1 | <100 | 31,382 | 136,945 | <100 | 164 | 9,363 | <5 | 58 | 4,666 |
| | 3 | <100 | 37,245 | 65,499 | <100 | 260 | 11,332 | <5 | 40 | 5,381 |
| | 4 | <100 | 37,731 | 135,539 | <100 | 176 | 7,566 | <5 | <5 | 8,163 |
| | 5 | <100 | 43,943 | 134,255 | <100 | 195 | 9,970 | <5 | 6 | 7,401 |
| | 6 | <100 | 28,668 | 49,032 | <100 | 263 | 12,425 | <5 | 19 | 3,199 |
| | 7 | <100 | 63,053 | 260,311 | <100 | 151 | 14,237 | <5 | 23 | 9,513 |
| | 8 | <100 | 86,215 | 235,759 | <100 | 453 | 13,387 | <5 | 37 | 3,164 |
| | GMT | | 43,652 | 125,529 | | 222 | 10,956 | | 20 | 5,467 |
| MBP::VP6$_{BC}$ | 1 | <100 | 100 | 66,661 | <100 | <100 | 1,470 | <5 | 13 | 1,859 |
| | 2 | <100 | 100 | 109,867 | <100 | <100 | 4,327 | <5 | <5 | 3,872 |
| | 3 | <100 | 100 | 72,780 | <100 | <100 | 9,919 | <5 | 7 | 1,762 |
| | 4 | <100 | 100 | 58,668 | <100 | <100 | 3,498 | <5 | 6 | 2,926 |
| | 5 | <100 | 100 | 60,548 | <100 | <100 | 8,879 | <5 | <5 | 6,602 |
| | 6 | <100 | 100 | 83,420 | <100 | <100 | 4,054 | <5 | <5 | 4,608 |
| | 7 | <100 | 100 | 126,528 | <100 | <100 | 11,466 | <5 | <5 | 7,061 |
| | 8 | <100 | 100 | 52,172 | <100 | <100 | 3,884 | <5 | 7 | 3,171 |
| | GMT | | | | | | 4,938 | | 6 | 3,551 |
| MBP::VP6$_{CD}$ | 2 | <100 | 155,158 | 420,416 | <100 | 957 | 266,389 | <5 | 60 | 18,245 |
| | 3 | <100 | 137,463 | 701,792 | <100 | 551 | 218,600 | <5 | 85 | 16,452 |
| | 4 | <100 | 137,679 | 524,277 | <100 | 696 | 65,597 | <5 | 84 | 11,163 |
| | 5 | <100 | 149,834 | 598,649 | <100 | 727 | 16,722 | <5 | 83 | 3,504 |
| | 6 | <100 | 89,976 | 212,449 | <100 | 979 | 54,195 | <5 | 157 | 9,141 |
| | 7 | <100 | 179,669 | 354,013 | <100 | 730 | 67,505 | <5 | 100 | 16,652 |
| | 8 | <100 | 87,840 | 555,205 | <100 | 508 | 67,927 | <5 | 15 | 7,249 |
| | GMT | | 129,920 | 452,205 | | 716 | 76,880 | | 70 | 10,377 |

Numbers of <100 u/ml indicate that no serum rotavirus IgG or IgA was detected.

avidin-biotin (Vector Laboratories), and o-phenylenediamine substrate (Sigma Chemical Co.). Color development was stopped after fifteen minutes with 1 M $H_2SO_4$ and the $A_{490}$ was measured. Titers of rotavirus IgG or IgA, expressed as units/ml, were determined from a standard curve generated by subtraction of the average $A_{490}$ values of the duplicate cell lysate wells from the average of the wells coated with EDIM lysate. For determination of stool rotavirus IgA, two stool pellets were collected into 0.5 ml of EBSS, homogenized, and centrifuged (1500 g, 5 min). Stool rotavirus IgA was then measured by the method described above.

Measurement of prechallenge VP6-specific antibody titers (Table 7) revealed that the AB and CD fragments induced high titers of serum IgG (GMT=43,625 U/ml and 129,920 U/ml respectively). Fragments AB and CD also induced serum IgA (GMT=222 U/ml and 716 U/ml respectively). Unexpectedly, no specific serum IgG or serum IgA (titer<100) could be detected in MBP::VP6$_{BC}$-inoculated mice by EIA (Table 7). Interestingly, the CD Example 13

Western Blot Analysis

Serum samples from mice immunized with vaccines were analyzed for rotavirus protein-specific antibodies by Western blot analyses. Cesium chloride gradient-purified rotavirus particles were subjected to SDS-polyacrylamide gel electrophoresis. Separated rotavirus proteins were blotted to a nitrocellulose sheet and cut into strips each of which contained 3 μg of rotavirus proteins. The strips were blocked with 5% skim milk in Tris-HCl buffer (TBS, 50 mM Tris-HCl, pH 7.5, 0.9% NaCl). The strips were then incubated with antisera obtained from immunized mice. After washing with 0.1% Tween-20 in TBS, the strips were incubated with goat anti-mouse IgG conjugated to alkaline phosphatase (Life Technologies, Gaithersburg, Md.). The strips were washed with TBS and then incubated with 4-chloro-3-indolylphosphate and nitroblue tetrazolium (Life Technologies, Gaithersburg, Md.) to visualize bound antibodies.

Western blot analyses confirmed that no specific antibodies could be detected in BMP::VP6$_{BC}$-immune sera (FIG. 6).

Example 14

Protection against EDIM Shedding by MBP::VP6 in μMt Mice

B-cell deficient μMT mice were also vaccinated intranasally with two doses (8.8 μg/dose) of MBP::VP6 with LT. As expected, no rotavirus IgG, IgA or IgM was detected in the sera of any of these mice during this study. Analyses of virus shedding indicated that the subunit vaccine was as protective in these mice as was found with immunologically normal BALB/c mice (Table 8). This finding suggested that the vaccine could induce protection by a mechanism that did not require rotavirus antibodies. The mechanism was therefore not antibody dependent.

sion of MBP fusion proteins. These plasmids expressed MBP::VP6$_{CD1}$ containing amino acids 197 to 263, MBP::VP6$_{CD2}$ containing amino acids 244 to 310, MBP::VP6$_{CD3}$ containing amino acids 291 to 351, and MBP::VP6$_{CD4}$ containing amino acids 332 to 397 (FIG. 8).

Recombinant plasmids were transformed into E. coli. White colonies of bacteria containing recombinant plasmids on agar plates were then identified in the presence of IPTG and X-gal, and selected for further screening by PCR for gene identity and orientation. Recombinant bacteria were grown as described previously for pMAL-c2/EDIM6. An overnight culture was grown (37° C.; shaken at 215 rpm) in rich broth (tryptone, 10 gm; yeast extract, 5 gm; NaCl, 5 gm; glucose, 2 gm; and ampicillin, 100 mg per liter). On the following day, 10 ml of overnight culture were inoculated into 1 liter of rich broth. The culture was grown until the A$_{600}$ reached ~0.6. IPTG was added (0.3 mM) to induce expression of the fusion protein. Growth was then continued

TABLE 8

Rotavirus shed in B-cell deficient μMt mice challenged with EDIM after immunization with 2 doses of MBP::VP6

| Vaccine | Mouse Number | Day 2 | 3 | 4 | 5 | 6 | 7 | 8 | 9 | Mean shedding per mouse per day | Reduction in shedding relative to control |
|---|---|---|---|---|---|---|---|---|---|---|---|
| None | 1 | 1 | 11 | 39 | 197 | 114 | 10 | 0 | 0 | | |
| | 2 | 98 | 3277 | 3579 | 2256 | 2760 | 1111 | 173 | 0 | | |
| | 3 | 19 | 152 | 564 | 573 | 526 | 84 | 16 | 0 | | |
| | 4 | 10 | 946 | 3588 | 2819 | 2065 | 1051 | 25 | 5 | | |
| | 5 | 32 | 1227 | 2762 | 3271 | 92 | 20 | 0 | 0 | | |
| | 6 | 377 | 505 | 1434 | 398 | 492 | 14 | 0 | 0 | 764.44 | |
| | 1 | 10 | 0 | 0 | 0 | 0 | 0 | 0 | 0 | | |
| | 2 | 3 | 0 | 0 | 0 | 0 | 0 | 0 | 0 | | |
| | 3 | 0 | 0 | 0 | 0 | 0 | 0 | 0 | 0 | | |
| | 4 | 0 | 0 | 0 | 0 | 0 | 0 | 0 | 0 | | |
| | 5 | 3 | 0 | 0 | 0 | 0 | 0 | 0 | 0 | | |
| | 6 | 38 | 23 | 17 | 9 | 7 | 0 | 0 | 0 | 2.40 | 99.69% |

Note: Shedding values of 0 indicate that shedding was below the limit of detection at 3 ng/ml.

In Example 15, two approaches were used to locate and characterize the protective epitopes in VP6. One approach was to immunize with expressed chimeric MBP proteins containing fragments of VP6. The other approach was to immunize with synthetic peptides. The goal was to identify the minimal protective epitopes which may possibly be incorporated into a subunit vaccine.

Example 15

Construction and Testing of Recombinant pMAL-c2 Plasmids Expressing Fragments of BMP::VP6$_{CD}$ Minimal Subunit Vaccine Because the C-terminal 50% of VP6 CD region could induce the same level of protection as the entire VP6 protein, the protective domains of this 201-amino acid portion of VP6 were further mapped. Four overlapping regions of the C-terminal CD region of the VP6 gene were cloned into pMAL-c2 (FIG. 7). The specific primers that were used for construction of these plasmids are summarized in Table 9. As described previously, cDNAs were inserted into the restriction site Xmn I of pMAL-c2, placing the inserted sequences downstream from the E. coli Mal E gene, which encodes maltose binding protein (MBP), resulting in expresfor 3 hours. Nucleotide sequencing was used to ultimately confirm the authenticity of the rotavirus gene sequences.

The 201-amino acid long CD region of VP6 could induce the same level of protection as the entire VP6 protein. To further map protective domains in this portion of VP6, four overlapping regions are cloned into pMAL-c2. The sub-regions are designated CD1, CD2, CD3 and CD4, and contain 67, 67, 61 and 66 amino acids, respectively (FIG. 7 & Table 9). The fusion proteins MBP::VP6$_{CD1}$, MBP::VP6$_{CD2}$, MBP::VP6$_{CD3}$ and MBP::VP6$_{CD4}$ containing these sub-regions are purified as described in Example 2 and tested for their protective efficacies.

Vaccination was performed as described in Example 15, Fine Mapping of Protective Epitopes using Synthetic Peptides. The protective efficiencies of various peptides were 88, 85, 19, and 92% for CD1, CD2, CD3, and CD4, respectively. These results show that peptides CD1, CD2, and CD4 have utility as vaccine components.

TABLE 9

Primers used to clone pMAL-c2/EDIM6$_{CD1}$, pMAL-c2/EDIM6$_{CD2}$, pMAL-c2/EDIM6$_{CD3}$ and pMal-c2c2/EDIM6$_{CD4}$

| Plasmid | Name of fusion protein | Primers |
|---|---|---|
| pMAL-c2/EDIM6$_{CD1}$ | MBP::VP6$_{CD1}$ | Forward primer: atg gat gtg ctg tac tct atc SEQ. I.D. NO. 7 |
| | | Reverse primer: tca gaa ctc aac ttc tac att att tgg SEQ. I.D. NO. 8 |
| pMAL-c2/EDIM6$_{CD2}$ | MBP::VP6$_{CD2}$ | Forward primer: gca act aca tgg tac ttc aac cca SEQ. I.D. NO. 9 |
| | | Reverse primer: tca att tgg gaa aag tgc agt cac tgc SEQ. I.D. NO. 10 |
| pMAL-c2/EDIM6$_{CD3}$ | MBP::VP6$_{CD3}$ | Forward primer: tca ttt caa ttg atg aga ccg cca SEQ. I.D. NO. 11 |
| | | Reverse primer: tca ttg tct gac tga cgt cac att ggc SEQ. I.D. NO. 12 |
| pMAL-c2/EDIM6$_{CD4}$ | MBP::VP6$_{CD4}$ | Forward primer: gaa tca gtt ctc gcg gat gca agt SEQ. I.D. NO. 13 |
| | | Reverse primer: tca ctt tac cag cat gct tct aat SEQ. I.D. NO. 14 |

Fine Mapping of Protective Epitopes using Synthetic Peptides

This approach was used to determine the smallest subunit vaccine possible. Synthetic peptides were designed to identify the protective domain(s) in the carboxyl-terminal half or CD region of VP6. A series of 11 overlapping peptides (Table 10) were synthesized by Quality Controlled Biochemicals, Inc (Hopkinton, Mass.). The synthetic peptides were on a Perkin Elmer 9050 peptide synthesizer or were synthesized manually. The well-established solid phase method was employed utilizing orthogonally protected amino acids. Cleavage and deprotection were done in aqueous trifluoroacetic acid. These overlapping peptides contained between 18 and 31 amino acids. All 11 peptides were tested as immunogens with LT(R192G).

Six-week-old rotavirus antibody-free female BALB/c mice (Harlan Sprague) and B-cell deficient μMt mice were used for vaccination. Blood and stool specimens were collected from the animals prior to vaccination. Animals were immunized intranasally with 8.8 μg of fusion proteins or 50 μg of synthetic peptides in a 50-μl volume. Animals receiving either two or three doses were immunized at biweekly intervals. The adjuvant E. coli LT(R192G) (10 μg supplied by Dr. Clements of Tulane University) was coadministered with the test vaccine.

Four weeks after the last immunization animals were bled and stool specimens were collected to measure antibody response. Each animal was challenged with a 100 ID$_{50}$ dose, which is equivalent to $4 \times 10^4$ ffu of EDIM virus, passage 9. Two stool pellets were collected into 1.0 ml of Earle's balanced salt solution (EBSS) from each mouse for seven or more days and stored at −20° C. Rotavirus antigen was measured in the stool by EIA to determine shedding (See Example 7). Twenty-one days after challenge, sera and stool specimens were obtained again to measure antibody responses.

The protective efficacies of seven peptides (3, 5, 6, 7, 9, 10, and 11) were first examined in BALB/c mice. It was found that two immunizations [50μg with 10 μg of LT(R192G)] with peptides 6, 11, or 3 induced a mean reduction in rotavirus shedding of 88, 64, and 57% respectively (Table 15, P<0.001). The other 4 peptides did not elicit protection. Peptide 6, a 25 mer, contains a 14-amino acid sequence RLSFQLMRPPNMTP that has been identified by a proliferation assay to be an H-2$^d$ CD4 epitope (Banos, et al., J Virol. 71:419–426, 1997). This 14 mer peptide, tentatively called 6–14, was also synthesized. Experiments using this 14 mer indicated that it provided comparable protection to that of peptide 6 in H-2$^d$ BALB/c mice.

The protective efficacies of peptide 1, 2, and 4 were tested. Peptides 2 and 4 were found to be 70 and 77% protective, respectively. The excellent protection observed with 6 of the peptides demonstrated that the maltose-binding protein is not required for induction of protection. These findings were confirmed with peptides 2 and 4. These results suggest the possibility of an alternative or supplemental vaccine strategy, i.e. a multi-peptide vaccine, which can be formulated from a selection of protective epitopes.

Subsequently, B-cell deficient μMt (H-2$^b$) mice are used to determine whether or not peptide(s)-induced antibodies are involved in protection.

TABLE 10

Synthetic peptides for mapping protective domains in the CD region of VP6

| Peptide Number | Sequence | SEQ. I.D. NO. |
|---|---|---|
| #1 | CAINAPANIQQFEHIVQLRRVLTTA | SEQ. I.D. No. 15 |
| #2 | PDAERFSFPRVINSADGA | SEQ. I.D. No. 16 |
| #3 | FSFPRVINSADGATTWYFNPVILRPNNVEV | SEQ. I.D. No. 17 |
| #4 | FNPVILRPNNVEVEFLLNGQVINTYQARF | SEQ. I.D. No. 18 |
| #5 | NGQVINTYQARFGTIVARNFDTIRLSFQLM | SEQ. I.D. No. 19 |
| #6 | RNFDTIRLSFQLMRPPNMTPAVTAL | SEQ. I.D. No. 20 |

TABLE 10-continued

Synthetic peptides for mapping protective domains in the CD region of VP6

| Peptide Number | Sequence | SEQ. I.D. NO. |
|---|---|---|
| #7 | MTPAVTALFPNAQPFEHHATVGLTLRIDSA | SEQ. I.D. No. 21 |
| #8 | HATVLTLRIDSAICESVLADASETMLANV | SEQ. I.D. No. 22 |
| #9 | VLADASETMLANVTSVRQEYAI | SEQ. I.D. No. 23 |
| #10 | QEYAIPVGPVFPPGMNWTDLITNYSPSRED | SEQ. I.D. No. 24 |
| #11 | TDLITNYSPSREDNLQRVFTVASIRSMLVK | SEQ. I.D. No. 25 |

Example 16

Mapping of Antibody Independent Epitopes Using µMt Mice

Understanding the mechanisms of protection is crucial to vaccine development. A unique observation obtained with chimeric vaccine, disclosed here, is that B-cell deficient µMt mice were found to be as well protected from shedding following vaccination with MBP::VP6 and LT(R192G) as immunologically normal BALB/c mice (See Example 14). This finding suggests that VP6 may induce completely antibody-independent protective immunity, a phenomenon that has not been reported previously for a rotavirus vaccine candidate. To locate the epitopes responsible for this protective mechanism, an experiment was conducted to initially examine the AB and CD peptides (i.e., MBP fusion proteins containing the first and second halves of VP6, respectively). Because peptide 6 provided excellent protection (88% reduction in shedding) and contains a putative CD4 epitope, groups of μMt mice were also inoculated with peptide 6 and 6–14, both of which contain the putative CD4 epitope.

Examples 17 and 18 describe further experiments to determine which T cells are involved in immunity.

Example 17

The Role of CD8 T Cells in MBP::VP6-mediated Immunity

Studies using rotavirus particles for intranasal immunization have shown that CD8 cells are not needed for protection. Experiments were performed to determine whether immunization with VP6 can also mediate CD8-independent protection. To achieve this goal, μMt mice were depleted of CD8 by injection with anti-CD8 antibodies. These mice were then immunized intranasally with MBP::VP6 and LT(R192G) and challenged with EDIM, as discussed above. The results showed that these animals were equally protected from viral infection following immunization whether or not CD8 cells were present or removed at the time of challenge.

Example 18

The Role of CD4 Cells in Protection

Based on results found with μMt mice, protection stimulated by VP6 was found not to be dependent on antibody production. Furthermore, protection following immunization with MBP::VP6 was not dependent on CD8 cells. This would leave CD4 cells as the most likely memory cells involved in protection. The importance of CD4 cells in protection following i.n. immunization using monoclonal antibody depletion as well as using genetically altered mice that lack CD4 cells was undertaken using the methods discussed above. In preliminary studies, it was found that i.n. immunization with double-layered rotavirus particles is much less protective in CD4-depleted or CD4 knock-out mice than in non-depleted or genetically normal mice. Similar results were obtained with CD4-depleted BALB/c mice immunized i.n. with the 6–14 peptide. It should be noted that peptide 6–14 discussed above provided nearly complete protection and this 14 amino acid peptide contains a known CD4 epitope.

Example 19

Rotavirus Fusion Protein Containing A Polymeric Histamine Fusion Partner (pMAL-c2X/EDIM6-6his)

Construction of pMAL-c2X/EDIM6-6his

To facilitate purification of a full length chimeric VP6, the plasmid pMAL-c2X (New England Biolabs, Beverly, Mass.) was used. The same construct can be used to express MBP::VP6::6Xhis or VP6::6Xhis. pMAL-c2X contains an Nde I site just 5' to the Mal E gene. This restriction site is one of 2 sites needed to delete the mal E sequence for the construction of pMAI-c2X/EDIM6-His6 that expresses the fusion protein 6his::VP6. The forward primer contains an Nde I site and a 5' terminal sequence of VP6 (nucleotides 4–21). The reverse sequence contains a stop codon (taa), 6 histidine-encoding codons and a 15-nucleotide VP6 carboxyl terminus sequence (Table 11). The newly added C-terminal 6Xhis fusion tag together with the N-terminal MBP enable the purification of the full-length VP6 using consecutive amylose resin and Talon (Palo Alto, Calif.) resin affinity chromatography. To create pMAL-c2X/EDIM6-6his, the recombinant plasmid was modified by digestion with Nde I and re-ligated to create the plasmid pc2X/EDIM6-6his. This plasmid expresses VP6::6Xhis that is devoid of MBP.

Purification of Full Length MBP::VP6::6Xhis

MBP::VP6::6Xhis was expressed as described above for the fusion peptides of CD and purified using amylose resin, also described (Example 15). It was found that the purified preparation also contained truncated MBP::VP6 lacking the C-terminal 6 histidine residues and varying lengths of the VP6 terminal. Full-length MBP::VP6::6Xhis was then purified from the truncated proteins using Talon affinity resin containing the divalent cobalt which selectively binds hexahistidines (Clontech, Palo Alto Calif.). To do this, the protein samples were denatured by adding guanidine-HCl, Tris-HCl (pH 8) and NaCl (final concentrations of 6 M, 50 mM and 400 mM, respectively). Talon resin was washed twice with sample lysis buffer (6 M guanidine-HCl, 400 mM NaCl, 50 mM Tris-HCl, pH 8). The protein solution was added to the washed Talon resin. The mixture was then gently agitated for at least 2 hours on a platform shaker. The resin was spun down in a centrifuge (700 g, 5 min) and the supernatant was discarded. The resin was washed by adding 10 bed-volumes of lysis buffer to the resin and the mixture was again agitated for 10 min on a platform shaker. The resin was spun down as before (700 g, 5 min) and the supernatant was discarded. The resin was washed in this way for a total of 4 times. The resin was resuspended in 1 bed-volume of lysis buffer and transferred to a 2-ml gravity-flow column. The resin was then washed twice with a wash buffer containing 8 M urea, 400 mM NaCl, 50 mM Tris-HCl, pH 8. The bound MBP::VP6::6Xhis was then eluted from the resin with elution buffer (6 M urea, 100 mM NaCl, 200 mM imidazole, 500 mM EDTA, 50 mM Tris-HCl, pH 8). The eluted protein was: subjected to buffer exchange to PBS by using Centriprep 50 filters (Amicon Inc., Beverly Mass.).

Western blot analysis of MBP::VP6::6Xhis. Purified MBP::VP6::6Xhis protein was analyzed by Western blot analysis to determine its purify. Purified MBP::VP6::6Xhis protein was subjected to SDS-polyacrylamide gel electrophoresis and blotted onto a nitrocellulose sheet. The sheet was blocked with 5% skim milk in Tris-HCl buffer (TVS; 50 mM Tris-HCl, pH 7.5, 0.9% NaCl). Duplicate sheets were then incubated with anti-MBP (New England Biolabs, Inc., Beverly Mass.) or anti-6Xhis (Santa Cruz, Calif.) sera. After washing with 0.1% Tween-20 in TBS, the strips were incubated with goat anti-rabbit IgG conjugated to alkaline phosphatase (Life Technologies, Gaithersburg, Md.). The strips were washed with TBS and then incubated with 4-chloro-3indolylphosphate and nitroblue tetrazolium (Life Technologies, Gaithersburg, Md.) to visualize bound antibodies. Preliminary experiments revealed a single protein corresponding to MBP::VP6::6Xhis that appeared to free of major contamination by truncated proteins.

Immunization of mice with MBP::VP6::6Xhis. Groups of 8 BALB/c mice have been immunized with 2 sequential doses (8.8 mg/dose) of the purified, doubly tagged VP6 protein and challenged with EDIM 1 month after the last immunization. Results from these experiments showed that mice immunized with this fusion protein were protected from rotaviral disease to a degree comparable to that found with MBP::VP6 immunized mice.

TABLE 11

Primers used to clone pMAL-c2X/EDIM6-6his

| Primer | Sequence |
|---|---|
| Forward | catatg[1] gac gtg ctg tac tct atc<br>SEQ. I.D. NO. 26 |
| Reverse | tta atgatgatgatgatg[2] ctt tac cag cat gct<br>SEQ. I.D. NO. 27 |

[1]NdeI restriction site is underlined
[2]codons for His

To analyze whether MBP is absolutely necessary for immunization, a VP6::6Xhis fusion protein was constructed. VP6::6Xhis, although still a fusion protein is considerably less bulky. Example 20 presents the construction and analysis of this protein.

Example 20

Recombinant Rotavirus Fusion Protein Replacing MBP with 6his

The construction of a recombinant rotavirus fusion protein using a fusion partner of 6 histidines rather than MBP is described below. Although MBP by itself did not induce protection or rotavirus-specific antibodies, it is not clear if it can modulate VP6-induced protective immunity. To determine whether MBP has any adjuvant effects on the protective efficacy of VP6, as well as to show the ability of other amino acid sequences to serve as fusion protein partners, a recombinant plasmid was constructed by first cloning VP6 into pMAL-c2X, as described above. This plasmid is identical to pMAL-c2 except that it contains a Nde I restriction site which, together with an engineered Nde I site (Table 11), allows the eventual deletion of the mal E sequence.

Characterization of the recombinant plasmid shows the authenticity of the coding region. The 6his::VP6 recombinant rotavirus fusion protein expresses well, compared to the expression levels of the other recombinant rotavirus fusion proteins. The presence of the 6his sequence may prevent the assembly of the recombinant rotavirus fusion protein into a multimeric form and facilitates the purification of the recombinant protein. The efficacy of 6his::VP6 to elicit a protective immune response from an individual immunized with a vaccine containing this protein is compared with that of MBP::VP6. The results of this comparison show that the two recombinant rotavirus fusion roteins are capable of eliciting protective immune responses.

Even though intranasal immunization with VP6 provided nearly complete protection against rotavirus shedding following a subsequent challenge with murine rotavirus, the duration of protection had not been examined. In Example 21 the duration of protection using the MBP::VP6 is presented.

Further experiments were performed to optimize vaccination using the present vaccines 21–24 present data analyzing duration, other mucosal routes, other adjuvants, effect of dosage on the immune response.

Example 21

Duration of Protection Experiments

In the typical immunization protocol, mice were challenged 1 month after the last immunization. For this study, the time between the last immunization and challenge was extended to 3 months to determine whether the degree of protection (quantity of virus shed after challenge) is reduced with time. Mice given two intranasal immunizations with MBP::VP6 (8.8 µg/dose) and LT(R129G) separated by a 2 week interval were found to be equally protected at 3 months (99.7%) or 1 month (97.8%) after the immunization (Table 12). This finding demonstrated that protection is not rapidly lost immunization, an important finding regarding the utility of VP6 as a vaccine candidate.

TABLE 12

Protection of BALB/c mice at 1 versus 3 months after i.n. immunization with 2 doses of MBP::VP6

|  | Mouse number | Day 1 | Day 2 | Day 3 | Day 4 | Day 5 | Day 6 | Day 7 | Shedding per mouse per day | % Reduction in shedding |
|---|---|---|---|---|---|---|---|---|---|---|
| 1 month | | | | | | | | | | |
| Unimmunized | 1 | 0 | 64 | 2,050 | 470 | 269 | 52 | 0 | 315 | |
|  | 2 | 0 | 92 | 1,508 | 185 | 159 | 32 | 0 | | |
|  | 3 | 0 | 103 | 272 | 194 | 196 | 9 | 0 | | |
|  | 4 | 0 | 18 | 3,740 | 1,132 | 603 | 88 | 0 | | |
|  | 5 | 0 | 18 | 1,051 | 78 | 61 | 23 | 0 | | |
|  | 6 | 0 | 59 | 2,761 | 222 | 86 | 23 | 0 | | |
|  | 7 | 0 | 8 | 169 | 238 | 66 | 55 | 0 | | |
|  | 8 | 0 | 0 | 59 | 1,026 | 290 | 105 | 0 | | |
| VP6 + LT (R192G) | 1 | 0 | 15 | 19 | 0 | 0 | 0 | 0 | 7 | 97.8 |
|  | 2 | 0 | 8 | 13 | 7 | 19 | 4 | 0 | | |
|  | 3 | 0 | 6 | 8 | 0 | 23 | 0 | 0 | | |
|  | 4 | 0 | 21 | 46 | 19 | 43 | 0 | 0 | | |
|  | 5 | 0 | 14 | 11 | 0 | 0 | 0 | 0 | | |
|  | 6 | 0 | 8 | 0 | 0 | 0 | 0 | 0 | | |
|  | 7 | 20 | 90 | 0 | 0 | 0 | 0 | 0 | | |
|  | 8 | 0 | 20 | 0 | 0 | 0 | 0 | 0 | | |
| 3 months | | | | | | | | | | |
| Unimmunized | 1 | 0 | 5 | 987 | 621 | 310 | 80 | 8 | 592 | 0 |
|  | 2 | 0 | 177 | 711 | 167 | 108 | 15 | 0 | | |
|  | 3 | 3 | 11 | 538 | 1,298 | 560 | 116 | 4 | | |
|  | 4 | 0 | 22 | 233 | 262 | 122 | 40 | 0 | | |
|  | 5 | 0 | 1,739 | 12,566 | 1,650 | 996 | 377 | 8 | | |
|  | 6 | 0 | 61 | 397 | 303 | 219 | 17 | 0 | | |
|  | 7 | 0 | 169 | 3,179 | 1,426 | 434 | 137 | 8 | | |
|  | 8 | 0 | 15 | 349 | 1,922 | 532 | 261 | 4 | | |
| VP6 + LT (R192G) | 1 | 0 | 15 | 0 | 0 | 0 | 0 | 0 | 2 | 99.7 |
|  | 2 | 0 | 0 | 10 | 0 | 0 | 0 | 0 | | |
|  | 3 | 3 | 0 | 0 | 0 | 0 | 0 | 0 | | |
|  | 4 | 0 | 19 | 17 | 0 | 0 | 0 | 0 | | |
|  | 5 | 0 | 0 | 9 | 4 | 0 | 0 | 0 | | |
|  | 6 | 0 | 0 | 0 | 0 | 0 | 0 | 0 | | |
|  | 7 | 0 | 6 | 0 | 0 | 0 | 0 | 0 | | |
|  | 8 | 0 | 9 | 0 | 0 | 0 | 0 | 0 | | |

Example 22

Induction of Protective Immunity by another Mucosal Route

To determine whether MBP::VP6 is protective if delivered by a mucosal route other than intranasally, groups of mice were immunized orally with 2 inoculations of MBP::VP6 (8.8 μg per inoculation), either with or without LT(R192G). Another group was immunized intranasally with this fusion protein and LT(R192G) for comparison. Immunized were challenged with murine rotavirus 1 month after the last immunization the percent reduction in viral shedding was calculated (Table 13). Oral immunization with MBP::VP6 and LT(R192G) induced good protection (85% reduction in shedding) but this reduction was significantly ($P<0.001$) less than after i.n. immunization (99%). Therefore, i.n. was more effective than oral immunization; however, it is possible that the two routes may be used concomitantly to increase protection, a possibility to be examined in future experimentation. Induction of protection by oral inoculation, as in the case of intranasal immunization, was dependent on the presence of LT(R192G), which reemphasized the requirement for an adjuvant to be used in conjunction with the VP6 vaccine.

TABLE 13

Protection of BALB/c mice by oral versus i.n. immunization with 2 doses of MBP::VP6

| Immunogen | Mouse number | Day 1 | Day 2 | Day 3 | Day 4 | Day 5 | Day 6 | Day 7 | Mean shedding per mouse per day | % Reduction in shedding |
|---|---|---|---|---|---|---|---|---|---|---|
| Oral | | | | | | | | | | |
| Unimmunized | 1 | 0 | 11 | 862 | 1,190 | 208 | 79 | 0 | 385 | |
|  | 2 | 0 | 363 | 3,491 | 592 | 508 | 62 | 0 | | |
|  | 3 | 0 | 220 | 2,491 | 846 | 184 | 116 | 4 | | |
|  | 4 | 0 | 85 | 943 | 490 | 184 | 221 | 24 | | |

TABLE 13-continued

Protection of BALB/c mice by oral versus i.n. immunization with 2 doses of MBP::VP6

| Immunogen | Mouse number | Day 1 | Day 2 | Day 3 | Day 4 | Day 5 | Day 6 | Day 7 | Mean shedding per mouse per day | % Reduction in shedding |
|---|---|---|---|---|---|---|---|---|---|---|
| | 5 | 0 | 62 | 740 | 584 | 110 | 146 | 0 | | |
| | 6 | 0 | 41 | 2,480 | 1,248 | 652 | 151 | 0 | | |
| | 7 | 0 | 6 | 242 | 663 | 118 | 108 | 0 | | |
| | 8 | 0 | 20 | 217 | 532 | 137 | 117 | 4 | | |
| VP6 | 1 | 0 | 381 | 4,579 | 412 | 308 | 44 | 0 | 571 | 0 |
| | 2 | 0 | 166 | 1,011 | 199 | 192 | 10 | 0 | | |
| | 3 | 5 | 893 | 1,532 | 260 | 184 | 6 | 0 | | |
| | 4 | 0 | 698 | 4,605 | 592 | 148 | 8 | 0 | | |
| | 5 | 0 | 244 | 1,894 | 575 | 120 | 34 | 0 | | |
| | 6 | 0 | 757 | 3,421 | 1,823 | 816 | 380 | 22 | | |
| | 7 | 0 | 16 | 478 | 430 | 189 | 86 | 16 | | |
| | 8 | | | | | | | | | |
| VP6 + LT(R192G) | 1 | 0 | 188 | 255 | 352 | 50 | 19 | 0 | 59 | 85 |
| | 2 | 0 | 75 | 102 | 3 | 0 | 10 | 0 | | |
| | 3 | 0 | 149 | 108 | 11 | 3 | 4 | 0 | | |
| | 4 | 0 | 132 | 156 | 43 | 11 | 14 | 0 | | |
| | 5 | 0 | 93 | 899 | 196 | 45 | 33 | 0 | | |
| | 6 | 0 | 14 | 6 | 0 | 0 | 0 | 0 | | |
| | 7 | 0 | 118 | 121 | 33 | 8 | 10 | 0 | | |
| | 8 | 10 | 25 | 15 | 0 | 0 | 0 | 0 | | |
| Intranasal | | | | | | | | | | |
| VP6 + LT(R192G) | 1 | 0 | 5 | 5 | 3 | 20 | 0 | 0 | 5 | 99 |
| | 2 | 0 | 0 | 8 | 0 | 0 | 0 | 0 | | |
| | 3 | 0 | 29 | 0 | 0 | 0 | 0 | 0 | | |
| | 4 | 0 | 16 | 5 | 0 | 0 | 0 | 0 | | |
| | 5 | 0 | 13 | 8 | 0 | 0 | 0 | 0 | | |
| | 6 | 0 | 68 | 26 | 3 | 0 | 0 | 0 | | |
| | 7 | 0 | 14 | 10 | 0 | 0 | 0 | 0 | | |
| | 8 | 0 | 7 | 0 | 0 | 23 | 0 | 0 | | |

Example 23

Effect of Different Adjuvants on Protection

Six-week-old rotavirus antibody-free female BALB/c mice (Harlan Sprague) and B-cell deficient μMt mice were used for vaccination. Blood and stool specimens were collected from the animals prior to vaccination. Animals were immunized orally or intranasally with 8.8 μg of fusion proteins. Animals, receiving either two or three doses were immunized at biweekly intervals. When adjuvants were coadministered with the test vaccine, $E.\ coli$ LT(R192G) (10 μg supplied by Dr. Clements of Tulane University), $V\ cholerae$ CT (10 mg Sigma Chemical Co., St. Louis, Mo.), poly[di(carboxylatophen-oxy)phosphazerie] (PCPP 50 μg, Avant Immunotherapeutics, Needham, Mass.) or QS-21 (20 μg Wyeth-Lederle Laboratories) was used.

Four weeks after the last immunization, animals were bled and stool specimens were collected to measure antibody response. Each animal was challenged with a 100 $ID_{50}$ dose, which is equivalent to $4 \times 10^4$ ffu, of EDIM virus passage 9. Two stool pellets were collected into 1.0 ml of Earle's balanced salt solution (EBSS) from each mouse for seven or more days and stored at −20° C. Rotavirus antigen was measured in the stool by EIA to determine shedding (See Example 7). Twenty-one days after challenge, sera and stool specimens were obtained again to measure antibody responses.

It had already been shown that cholera toxin (CT), which is biologically and functionally related to LT, could replace LT(R192G) as adjuvant. The effectiveness of other adjuvants (PCPP, QS-21) have now been examined. Groups of mice were vaccinated with 2 i.n. immunizations (two weeks apart) with MBP::VP6 and adjuvant [PCPP, QS-21 or LT(R192G)] (Table 14). The adjuvant PCPP conferred an 80% reduction in shedding when administered intranasally with MBP::VP6 but it was not effective when given orally. In contrast, 59% and 43% reductions were observed when QS-21 was included with MBP::VP6 for oral and intranasal inoculation, respectively. As previously observed, LT(R192G) provided 99% protection when given with the vaccine intranasally but was less protective (85%) when administered orally. These results indicate that the choice of adjuvant and the route of mucosal inoculation both impact the efficacy of the VP6 vaccine.

To search for other effective adjuvants, nucleic acid adjuvants (CpG DNA from CpG ImmunoPharmaceuticals, Wellesley, Mass.), double-stranded RNA, and the cholera toxin A1-based gene fusion protein CTA1-DD (Agren, et al. J Immunol 162:2432–2440, 1999), will be tested for their effectiveness in stimulating VP6-induced protective immunity.

TABLE 14

Effect of different adjuvants on oral and intranasal MBP::VP6-induced protection of BALB/c mouse

| Immunogen | Mouse number | Day 1 | Day 2 | Day 3 | Day 4 | Day 5 | Day 6 | Day 7 | Shedding per mouse per day | % Reduction in shedding |
|---|---|---|---|---|---|---|---|---|---|---|
| Intranasal | | | | | | | | | | |
| Unimmunized | 1 | 0 | 208 | 835 | 70 | 104 | 37 | 0 | 311 | |
| | 2 | 0 | 37 | 674 | 249 | 623 | 117 | 10 | | |
| | 3 | 0 | 88 | 2,838 | 685 | 1,686 | 588 | 31 | | |
| | 4 | 0 | 193 | 552 | 574 | 242 | 64 | 0 | | |
| | 1 | 0 | 20 | 420 | 540 | 247 | 207 | 5 | | |
| | 2 | 0 | 28 | 2,901 | 481 | 159 | 167 | 10 | | |
| | 3 | 0 | 19 | 962 | 198 | 134 | 59 | 13 | | |
| | 4 | 0 | 0 | 0 | 30 | 176 | 133 | 12 | | |
| VP6 + LT(R19 2G) | 1 | 0 | 0 | 0 | 0 | 0 | 0 | 0 | 2 | 99 |
| | 2 | 0 | 10 | 0 | 0 | 0 | 0 | 0 | | |
| | 3 | 0 | 13 | 0 | 0 | 0 | 0 | 0 | | |
| | 4 | 0 | 7 | 0 | 0 | 0 | 0 | 0 | | |
| | 5 | 7 | 8 | 0 | 0 | 0 | 0 | 0 | | |
| | 6 | 0 | 29 | 0 | 0 | 0 | 0 | 0 | | |
| | 7 | 0 | 14 | 5 | 0 | 0 | 0 | 0 | | |
| | 8 | 0 | 9 | 7 | 0 | 0 | 7 | 0 | | |
| VP6 + QS21 | 1 | 0 | 7 | 285 | 1,200 | 263 | 62 | 0 | 177 | 43 |
| | 2 | 0 | 47 | 570 | 200 | 365 | 19 | 0 | | |
| | 3 | 0 | 6 | 159 | 206 | 291 | 34 | 9 | | |
| VP6 + PCPP | 1 | 0 | 24 | 86 | 43 | 43 | 0 | 0 | 63 | 80 |
| | 2 | 0 | 97 | 220 | 138 | 324 | 14 | 0 | | |
| | 3 | 0 | 15 | 203 | 100 | 15 | 0 | 0 | | |
| | 4 | 0 | 51 | 260 | 21 | 97 | 0 | 0 | | |
| | 5 | 5 | 18 | 339 | 54 | 69 | 19 | 0 | | |
| | 6 | 6 | 189 | 76 | 29 | 42 | 0 | 0 | | |
| | 7 | 0 | 30 | 20 | 30 | 23 | 0 | 0 | | |
| | 8 | 14 | 200 | 193 | 221 | 250 | 0 | 0 | | |
| Oral | | | | | | | | | | |
| Unimmunized | 1 | 0 | 11 | 862 | 1,190 | 208 | 79 | 0 | 385 | |
| | 2 | 0 | 363 | 3,491 | 592 | 508 | 62 | 0 | | |
| | 3 | 0 | 220 | 2,491 | 846 | 184 | 116 | 4 | | |
| | 4 | 0 | 85 | 943 | 490 | 184 | 221 | 24 | | |
| | 5 | 0 | 62 | 740 | 584 | 110 | 146 | 0 | | |
| | 6 | 0 | 41 | 2,480 | 1,248 | 652 | 151 | 0 | | |
| | 7 | 0 | 6 | 242 | 663 | 118 | 108 | 0 | | |
| | 8 | 0 | 20 | 217 | 532 | 137 | 117 | 4 | | |
| VP6 + LT (R192G) | 1 | 0 | 188 | 255 | 352 | 50 | 19 | 0 | 59 | 85 |
| | 2 | 0 | 75 | 102 | 3 | 0 | 10 | 0 | | |
| | 3 | 0 | 149 | 108 | 11 | 3 | 4 | 0 | | |
| | 4 | 0 | 132 | 156 | 43 | 11 | 14 | 0 | | |
| | 1 | 0 | 93 | 899 | 196 | 45 | 33 | 0 | | |
| | 2 | 0 | 14 | 6 | 0 | 0 | 0 | 0 | | |
| | 3 | 0 | 118 | 121 | 33 | 8 | 10 | 0 | | |
| | 4 | 10 | 25 | 15 | 0 | 0 | 0 | 0 | | |
| VP6 + QS-21 | 1 | 0 | 0 | 56 | 169 | 20 | 37 | 6 | 156 | 59 |
| | 2 | 0 | 131 | 175 | 35 | 0 | 4 | 0 | | |
| | 3 | 0 | 25 | 505 | 801 | 115 | 47 | 0 | | |
| | 4 | 0 | 42 | 562 | 714 | 506 | 303 | 12 | | |
| | 1 | 0 | 0 | 546 | 269 | 55 | 14 | 0 | | |
| | 2 | 0 | 159 | 1,066 | 208 | 66 | 20 | 0 | | |
| | 3 | 0 | 36 | 627 | 378 | 34 | 39 | 0 | | |
| | 4 | 0 | 14 | 153 | 204 | 536 | 48 | 11 | | |
| VP6 + PCPP | 1 | 0 | 77 | 221 | 271 | 80 | 22 | 0 | 387 | 0 |
| | 2 | 0 | 279 | 665 | 3,227 | 91 | 485 | 0 | | |
| | 3 | 0 | 126 | 2,656 | 436 | 4,816 | 8 | 3 | | |
| | 4 | 0 | 128 | 375 | 124 | 33 | 14 | 0 | | |
| | 1 | 0 | 125 | 542 | 210 | 129 | 12 | 0 | | |
| | 2 | 0 | 48 | 2,249 | 145 | 22 | 8 | 0 | | |
| | 3 | 0 | 316 | 1,222 | 150 | 440 | 35 | 0 | | |
| | 4 | 0 | 75 | 1,033 | 302 | 440 | 27 | 3 | | |

TABLE 15

Induction of protection by i.n. vaccination with overlapping synthetic peptides of the CD region of VP6 with LT(R192G)

| Peptides | Mouse number | Day 1 | Day 2 | Day 3 | Day 4 | Day 5 | Day 6 | Day 7 | Shedding per mouse per day | % Reduction in shedding |
|---|---|---|---|---|---|---|---|---|---|---|
| Unimmunized | 1 | 0 | 10 | 187 | 418 | 333 | 102 | 0 | 225 | |
| | 2 | 0 | 54 | 238 | 444 | 129 | 80 | 0 | | |
| | 3 | 0 | 33 | 706 | 1,251 | 1,046 | 99 | 0 | | |
| | 4 | 0 | 15 | 312 | 297 | 291 | 52 | 0 | | |
| | 1 | 0 | 79 | 767 | 265 | 240 | 40 | 0 | | |
| | 2 | 0 | 47 | 429 | 860 | 589 | 409 | 0 | | |
| | 3 | 0 | 23 | 767 | 387 | 412 | 145 | 0 | | |
| | 4 | 0 | 19 | 202 | 264 | 218 | 354 | 0 | | |
| MBP::VP6CD | 1 | 7 | 16 | 0 | 0 | 0 | 0 | 0 | 3 | 99 |
| | 2 | 0 | 0 | 16 | 13 | 0 | 0 | 0 | | |
| | 3 | 5 | 19 | 0 | 0 | 0 | 0 | 0 | | |
| | 4 | 0 | 0 | 0 | 0 | 0 | 0 | 0 | | |
| | 1 | 0 | 10 | 5 | 11 | 0 | 0 | 0 | | |
| | 3 | 0 | 26 | 0 | 0 | 0 | 0 | 0 | | |
| | 4 | 0 | 0 | 19 | 0 | 0 | 0 | 0 | | |
| Peptide 3 | 1 | 0 | 21 | 300 | 86 | 24 | 17 | 0 | 96 | 57 |
| | 2 | 26 | 294 | 472 | 134 | 175 | 16 | 0 | | |
| | 3 | 15 | 144 | 207 | 148 | 37 | 17 | 0 | | |
| | 4 | 5 | 140 | 292 | 37 | 52 | 14 | 0 | | |
| | 1 | 10 | 129 | 362 | 598 | 395 | 23 | 0 | | |
| | 2 | 10 | 6 | 196 | 71 | 20 | 18 | 0 | | |
| | 3 | 11 | 90 | 53 | 9 | 15 | 11 | 0 | | |
| | 4 | 20 | 94 | 434 | 86 | 44 | 14 | 0 | | |
| Peptide 5 | 1 | 12 | 128 | 261 | 270 | 150 | 31 | 0 | 341 | 0 |
| | 3 | 15 | 84 | 1,162 | 687 | 276 | 44 | 0 | | |
| | 4 | 0 | 25 | 629 | 373 | 272 | 43 | 18 | | |
| | 1 | 4 | 70 | 630 | 268 | 767 | 45 | 9 | | |
| | 2 | 5 | 148 | 988 | 666 | 1,738 | 409 | 7 | | |
| | 3 | 25 | 167 | 2,684 | 982 | 1,437 | 102 | 0 | | |
| | 4 | 7 | 36 | 480 | 263 | 234 | 58 | 0 | | |
| Peptide 6 | 1 | 12 | 76 | 23 | 6 | 26 | 34 | 0 | 27 | 88 |
| | 2 | 0 | 40 | 71 | 27 | 24 | 43 | 0 | | |
| | 3 | 6 | 25 | 29 | 0 | 11 | 12 | 0 | | |
| | 4 | 0 | 97 | 38 | 9 | 23 | 24 | 0 | | |
| | 1 | 11 | 29 | 52 | 7 | 10 | 13 | 0 | | |
| | 2 | 23 | 22 | 22 | 45 | 39 | 13 | 0 | | |
| | 3 | 6 | 25 | 29 | 0 | 11 | 12 | 0 | | |
| | 4 | 0 | 97 | 38 | 9 | 23 | 24 | 0 | | |
| | 1 | 11 | 29 | 52 | 7 | 10 | 13 | 0 | | |
| | 2 | 23 | 22 | 22 | 45 | 39 | 13 | 0 | | |
| | 3 | 0 | 58 | 40 | 4 | 24 | 25 | 0 | | |
| | 4 | 0 | 21 | 264 | 76 | 35 | 20 | 0 | | |
| Peptide 7 | 1 | 24 | 110 | 279 | 49 | 88 | 25 | 0 | 185 | 18 |
| | 2 | 0 | 17 | 990 | 402 | 178 | 115 | 16 | | |
| | 3 | 0 | 164 | 555 | 117 | 90 | 42 | 0 | | |
| | 4 | 0 | 0 | 428 | 288 | 200 | 130 | 0 | | |
| | 1 | 7 | 123 | 1,845 | 144 | 35 | 53 | 0 | | |
| | 2 | 0 | 48 | 1,063 | 293 | 692 | 242 | 9 | | |
| | 3 | 0 | 45 | 401 | 110 | 77 | 32 | 0 | | |
| | 4 | 15 | 147 | 486 | 97 | 69 | 26 | 0 | | |
| Peptide 9 | 1 | 63 | 277 | 2,707 | 249 | 66 | 41 | 0 | 275 | 0 |
| | 2 | 0 | 235 | 2,131 | 1,024 | 510 | 53 | 8 | | |
| | 3 | 0 | 163 | 1,714 | 289 | 111 | 37 | 0 | | |
| | 4 | 0 | 38 | 275 | 118 | 31 | 12 | 0 | | |
| | 1 | 0 | 76 | 393 | 270 | 205 | 49 | 0 | | |
| | 2 | 20 | 148 | 939 | 371 | 149 | 14 | 0 | | |
| | 3 | 0 | 68 | 948 | 364 | 209 | 39 | 0 | | |
| | 4 | 0 | 152 | 385 | 265 | 158 | 34 | 0 | | |
| Peptide 10 | 1 | 0 | 134 | 906 | 177 | 77 | 30 | 0 | 1825 | 0 |
| | 2 | 0 | 22 | 998 | 1,921 | 1,067 | 186 | 0 | | |
| | 3 | 0 | 85 | 1,428 | 287 | 256 | 53 | 0 | | |
| | 4 | 0 | 13 | 226 | 296 | 317 | 62 | 0 | | |
| | 1 | 8 | 479 | 59,673 | 14,718 | 6,851 | 1,261 | 0 | | |
| | 2 | 0 | 110 | 985 | 1,379 | 669 | 96 | 0 | | |
| | 3 | 8 | 222 | 991 | 5,318 | 65 | 36 | 0 | | |
| | 4 | 6 | 168 | 209 | 286 | 85 | 24 | 0 | | |
| Peptide 11 | 1 | 0 | 54 | 277 | 47 | 23 | 30 | 0 | 80 | 64 |
| | 2 | 0 | 19 | 186 | 220 | 47 | 29 | 0 | | |
| | 3 | 0 | 17 | 297 | 136 | 51 | 30 | 0 | | |
| | 4 | 15 | 31 | 487 | 59 | 39 | 41 | 0 | | |
| | 1 | 0 | 49 | 294 | 230 | 98 | 36 | 0 | | |
| | 3 | 0 | 32 | 212 | 181 | 62 | 23 | 0 | | |

Example 24

Effect of Dosage on Protection

The effect of dosage (1.76 µg and 8.8 µg) on protection by i.n. immunization with MBP::VP6 and LT(R192G) was examined (Table 16). Although mice immunized with two 1.76 µg dosages plus LT(R192G) of chimeric VP6 appeared to be nearly as well protected as those administered two 8.8 µg-doses, (protective levels were 94 and 99%, respectively) the 94% protection level was significantly (P=0.0003) lower than the 99% protection level.

TABLE 16

Effect of 2 i.n. immunizations of 1.76 µg- or 8.8-µg dose of MBP::VP6 and LT(R192G) on protection of BALB/c mouse against EDIM infection

| Quantity of immunogen | # | Day 1 | Day 2 | Day 3 | Day 4 | Day 5 | Day 6 | Day 7 | Shedding per mouse per day | % Reduction in shedding |
|---|---|---|---|---|---|---|---|---|---|---|
| 0 µg | 1 | 0 | 11 | 862 | 1,190 | 208 | 79 | 0 | 385 | |
| | 2 | 0 | 363 | 3,491 | 592 | 508 | 62 | 0 | | |
| | 3 | 0 | 220 | 2,491 | 846 | 184 | 116 | 4 | | |
| | 4 | 0 | 85 | 943 | 490 | 184 | 221 | 24 | | |
| | 5 | 0 | 62 | 740 | 584 | 110 | 146 | 0 | | |
| | 6 | 0 | 41 | 2,480 | 1,248 | 652 | 151 | 0 | | |
| | 7 | 0 | 6 | 242 | 663 | 118 | 108 | 0 | | |
| | 8 | 0 | 20 | 217 | 532 | 137 | 117 | 4 | | |
| 8.8 µg | 1 | 0 | 5 | 5 | 3 | 20 | 0 | 0 | 5 | 99 |
| | 2 | 0 | 0 | 8 | 0 | 0 | 0 | 0 | | |
| | 3 | 0 | 29 | 0 | 0 | 0 | 0 | 0 | | |
| | 4 | 0 | 16 | 5 | 0 | 0 | 0 | 0 | | |
| | 5 | 0 | 13 | 8 | 0 | 0 | 0 | 0 | | |
| | 6 | 0 | 68 | 26 | 3 | 0 | 0 | 0 | | |
| | 7 | 0 | 14 | 10 | 0 | 0 | 0 | 0 | | |
| | 8 | 0 | 7 | 0 | 0 | 23 | 0 | 0 | | |
| 1.76 µg | 1 | 0 | 24 | 13 | 4 | 29 | 11 | 0 | 25 | 94 |
| | 2 | 6 | 32 | 80 | 0 | 0 | 3 | 0 | | |
| | 3 | 0 | 40 | 74 | 3 | 15 | 5 | 0 | | |
| | 4 | 0 | 143 | 18 | 0 | 116 | 0 | 0 | | |
| | 5 | 0 | 47 | 113 | 6 | 48 | 6 | 0 | | |
| | 6 | 0 | 72 | 9 | 19 | 92 | 17 | 0 | | |
| | 7 | 0 | 21 | 25 | 0 | 22 | 0 | 0 | | |
| | 8 | 6 | 76 | 61 | 0 | 134 | 0 | 0 | | |

Although murine and human rotavirus VP6 proteins are highly homologous (see Example 30) it may be advantageous to have and use the human rotavirus VP6 protein for vaccination. Example 25 outlines the steps taken to clone the human rotavirus VP6.

Example 25

Expression of Human Rotavirus VP6

A VP6 protein from a human rotavirus strain is cloned and expressed as a fusion protein for development of a vaccine candidate to be tested in mice and humans. VP6 from human rotavirus strain CJN is cloned and its nucleotide sequence determined using standard techniques well known in the art. See *Current Protocols in Molecular Biology*, Eds. Ausubel, et al., John Wiley & Sons, Inc. The chimeric protein is tested in the mouse model to establish that a human VP6 protein from a group A virus can cross-protect against a heterologous group A (mouse EDIM) rotavirus. This human VP6 vaccine is tested in gnotobiotic pigs that have an immunological system similar to that of humans. This pig model allows for the testing of whether mouse or human VP6 can protect against human rotaviruses. The protein is used in subsequent human trials.

Examples 26–29 provide outlines of vaccine trials in humans and various uses of the vaccine. Example 30 provides a way of testing which human haplotype(s) will be protective.

Example 26

Human Vaccine Trial

A statistically significant number of volunteers are enrolled in a study to test the safety and efficacy of the full-length, peptide, or chimeric rotavirus fusion protein vaccine compositions of the present invention. A geographical location or locations for the test is selected on the basis that the area is known to have been the site of past rotavirus outbreaks. The ratio of vaccine to placebo groups is randomized to result in a range from at least 1:1 to no more than 2:1 ratio within the group. This randomization is designed to provide appropriately large groups for statistical analysis of the efficacy of the vaccine.

The vaccine composition to be used in this study will be one containing the chimeric rotavirus fusion protein comprising VP6 and MBP, the full-length VP6 alone or in combination with a further rotavirus protein, or single or multiple peptide vaccines. The vaccine composition will consist of a sufficiently high concentration of rotavirus protein so as to be effective to induce a protective immune response when the composition is administered parenterally or mucosally. Parenteral administration will preferably be via intramuscular injection. In both cases any of the adjuvants which are disclosed in the specification can be used.

The chimeric fusion protein is prepared according to the Examples described above. The placebo will consist of an equal volume of buffered saline and is also to be given mucosally or parenterally. Vaccine and placebo are supplied as individual doses that are stored at −20° C. and thawed immediately prior to use.

To determine the amount of vaccine necessary, different concentrations will be administered experimentally to a mouse. An effective concentration will be extrapolated and a comparable amount used in human subjects.

Blood samples are collected from all of the subjects for use in various laboratory assays. For example, enzyme immunoassay may be performed to evaluate the extent of the immune response elicited in each of the vaccinated individuals in response to the vaccine or placebo administered. Such techniques are well known in the art.

Individuals participating in this study are chosen who are healthy at the time of vaccination with either the test vaccine or the placebo. Test subjects are assigned to receive vaccine or placebo in a double-blind fashion using a block randomization scheme. An appropriate number of doses are administered over a given period of time, e.g., two months, to elicit an immune response.

Study participants are monitored throughout the following year to determine the incidence of rotavirus infection and the subsequent development of disease conditions. Participating subjects are contacted on a periodic basis during this period to inquire about symptoms of rotaviral disease, both in the test subject and in the subject's community. Local epidemiological surveillance records may also be accessed.

The results of the above described study are assessed using standard statistical methods. The vaccine is well tolerated at the effective dose. The epidemic curves of outbreaks of rotavirus in the geographic areas tested will be assessed and the distribution of episodes of rotaviral disease will be established. The incidence of rotavirus caused disease in immunized individuals will be reduced to a statistically significant extent as compared to those individuals receiving the placebo.

Example 27

Maternal Immunization and Passive Immunity in Nursing Infants

In this example maternal immunization is used to induce a protective immune response in women of child bearing age which in turn passively protects nursing infants from rotavirus caused disease.

A woman of child bearing age is selected for immunization with the full-length, subunit, VP6 fragment, or VP6-fusion protein of the present invention. The woman is immunized parenterally.

Route of administration and the effective amount will be as discussed in Example 26.

Example 28

Infant and Maternal Immunization as a Method to Augment Infant Protection

Infants are immunized with a rotaviral protein of the present invention. The immunization is carried out by any route that results in the generation of a protective immune response directed against the rotaviral fusion protein immunogen, particularly intramuscularly. Route of administration and the effective amount will be as discussed in Example 26. Ideally, the resulting immune response will protect the infant from subsequent rotavirus challenge.

To augment the immunization of the infant, the mother or nursing female would is also immunized with the rotaviral protein vaccine of the present invention. Immunization is contemplated by any route that results in the generation of an immune response on the part of the immunized female, particularly intramuscularly. This immunization results in a protective immune response being generated on the part of the immunized mother. What is required is an immune response (soluble immunological factors) is induced against the rotaviral fusion protein. Those immunological factors should also be present in the milk generated by the immunized female during lactation. Accordingly, the nursing female may be immunized before nursing has begun.

The present invention contemplates a cooperative interaction between the immunized immune system of the infant and that of the immunized nursing female. In the interim between the time of infant immunization and the generation of an immune response, the passive transmission of immunity from the milk of the mother will protect the infant from rotavirus infection.

Example 29

Booster Immunization with a Subunit Vaccine to Augment Protection Obtained from Other Mono or Multivalent Rotavirus Vaccines In this Example an individual is first immunized with a traditional monovalent or multivalent rotavirus vaccine. Example of such vaccines may be found in U.S. Pat. Nos. 4,927,628 and 5,626,851. Once an immune response has been mounted to this vaccine, rotaviral fusion proteins of the present invention may be used as a subsequent booster to strengthen the immune response created by the first immunization. Route of administration and the effective amount will be as discussed in Example 26.

Example 30

Human T Cell Proliferation Studies

VP6 is extremely conserved among human rotavirus strains, and between human and animal rotaviruses (90–95% amino acid identity). In spite of the known HLA polymorphism, it is anticipated that human vaccines will generate protective immunity following i.n. vaccination with full-length VP6, possibly through responses to different CD4 epitopes which are conserved within multiple rotavirus strains and the degeneracy of T cell recognition of different HLA-peptide complexes. As already mentioned, BALB/c and $\mu$Mt mice, which possess different H-2 molecules (H-$2^d$ and H-$2^b$, respectively) on their T cells, are equally protected by MBP::VP6. To investigate whether humans with different haplotypes (HLA molecules) can be protected, one well-established approach to determine the presence of antigen-specific T cells is to perform proliferation assays. Such an assay may entail the following: blood is collected from a cross-section of subjects in a community and isolation of their peripheral blood mononuclear cells (PBMC) are isolated. PBMC are exposed in vitro to chimeric mouse or human MBP::VP6 or synthetic peptides. PMBC from individuals with the ability to generate VP6-specific T cell responses will proliferate. Proliferation of specific cells is detected by incorporation of $^3$H-thymidine or using a non-radioactive proliferation assay (e.g. Molecular Probes, Eugene Oreg.). Information from this experiment allows for further modification of the VP6 vaccine to ensure protection of the population targeted for vaccination.

What is claimed is:

1. A composition comprising a rotavirus VP6 protein or a COOH-terminal fragment thereof, and an adjuvant in a pharmaceutical carrier, wherein said adjuvant is effective in combination with said VP6 protein or COOH-terminal fragment thereof to generate a disease-reducing response to rotavirus infection in a mammal, wherein said VP6 protein or COOH-terminal fragment thereof is not assembled into a viral particle.

2. The composition of claim 1, wherein said VP6 protein is derived from a human rotavirus strain.

3. The composition of claim 1, wherein said adjuvant is selected from the group consisting of: cholera toxin (CT) and *E. coli* heat-labile toxin (LT).

4. The composition of claim 1, wherein said adjuvant is selected from the group consisting of PCPP, QS-21, QS-7, CTA1-DD, CpG DNA, and double-stranded RNA (dsRNA).

5. The composition of claim 1, wherein said composition is adapted for administration by a route selected from the group consisting of intramuscular administration, intranasal administration, oral administration, transdermal administration, and transmucosal administration.

6. The composition of claim 1, wherein said fragment comprises $VP6_{CD}$.

7. The composition of claim 1, wherein said composition comprises a fragment of said VP6 protein, said fragment having a molecular weight less than about 24 kD.

* * * * *

SEQUENCE LISTING

<160> NUMBER OF SEQ ID NOS: 25

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
atggatgtgc tgtactctat c                                             21

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
tcacgagtag tcgaatcctg caac                                          24

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
atggatgaaa tgatgcgaga gtca                                          24

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
tcagaatggc ggtctcatca attg                                          24

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
tgcgcaatta atgctccagc t                                             21

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
tcactttacc agcatgcttc taat                                          24

<210> SEQ ID NO 7
<211> LENGTH: 21

```
<212> TYPE: DNA
<213> ORGANISM: Artificial Sequence
<220> FEATURE:
<223> OTHER INFORMATION: primer

<400> SEQUENCE: 7
atggatgtgc tgtactctat c                                          21

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
tcagaactca acttctacat tatttgg                                    27

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gcaactacat ggtacttcaa ccca                                       24

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
tcaatttggg aaaagtgcag tcactgc                                    27

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
tcatttcaat tgatgagacc gcca                                       24

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
tcattgtctg actgacgtca cattggc                                    27

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
```

-continued

```
gaatcagttc tcgcggatgc aagt                                            24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
tcactttacc agcatgcttc taat                                            24

<210> SEQ ID NO 15
<211> LENGTH: 25
<212> TYPE: PRT
<213> ORGANISM: Rotavirus VP6 fragment

<400> SEQUENCE: 15

Cys Ala Ile Asn Ala Pro Ala Asn Ile Gln Gln Phe Glu His Ile Val
 1               5                  10                  15

Gln Leu Arg Arg Val Leu Thr Thr Ala
            20                  25

<210> SEQ ID NO 16
<211> LENGTH: 18
<212> TYPE: PRT
<213> ORGANISM: Rotavirus VP6 fragment

<400> SEQUENCE: 16

Pro Asp Ala Glu Arg Phe Ser Phe Pro Arg Val Ile Asn Ser Ala Asp
 1               5                  10                  15

Gly Ala

<210> SEQ ID NO 17
<211> LENGTH: 30
<212> TYPE: PRT
<213> ORGANISM: Rotavirus VP6 fragment

<400> SEQUENCE: 17

Phe Ser Phe Pro Arg Val Ile Asn Ser Ala Asp Gly Ala Thr Thr Trp
 1               5                  10                  15

Tyr Phe Asn Pro Val Ile Leu Arg Pro Asn Asn Val Glu Val
            20                  25                  30

<210> SEQ ID NO 18
<211> LENGTH: 29
<212> TYPE: PRT
<213> ORGANISM: Rotavirus VP6 fragment

<400> SEQUENCE: 18

Phe Asn Pro Val Ile Leu Arg Pro Asn Asn Val Glu Val Glu Phe Leu
 1               5                  10                  15

Leu Asn Gly Gln Val Ile Asn Thr Tyr Gln Ala Arg Phe
            20                  25

<210> SEQ ID NO 19
<211> LENGTH: 30
<212> TYPE: PRT
<213> ORGANISM: Rotavirus VP6 fragment

<400> SEQUENCE: 19

Asn Gly Gln Val Ile Asn Thr Tyr Gln Ala Arg Phe Gly Thr Ile Val
 1               5                  10                  15
```

-continued

```
Ala Arg Asn Phe Asp Thr Ile Arg Leu Ser Phe Gln Leu Met
            20                  25                  30

<210> SEQ ID NO 20
<211> LENGTH: 25
<212> TYPE: PRT
<213> ORGANISM: Rotavirus VP6 fragment

<400> SEQUENCE: 20

Arg Asn Phe Asp Thr Ile Arg Leu Ser Phe Gln Leu Met Arg Pro Pro
 1               5                  10                  15

Asn Met Thr Pro Ala Val Thr Ala Leu
            20                  25

<210> SEQ ID NO 21
<211> LENGTH: 30
<212> TYPE: PRT
<213> ORGANISM: Rotavirus VP6 fragment

<400> SEQUENCE: 21

Met Thr Pro Ala Val Thr Ala Leu Phe Pro Asn Ala Gln Pro Phe Glu
 1               5                  10                  15

His His Ala Thr Val Gly Leu Thr Leu Arg Ile Asp Ser Ala
            20                  25                  30

<210> SEQ ID NO 22
<211> LENGTH: 29
<212> TYPE: PRT
<213> ORGANISM: Rotavirus VP6 fragment

<400> SEQUENCE: 22

His Ala Thr Val Leu Thr Leu Arg Ile Asp Ser Ala Ile Cys Glu Ser
 1               5                  10                  15

Val Leu Ala Asp Ala Ser Glu Thr Met Leu Ala Asn Val
            20                  25

<210> SEQ ID NO 23
<211> LENGTH: 22
<212> TYPE: PRT
<213> ORGANISM: Rotavirus VP6 fragment

<400> SEQUENCE: 23

Val Leu Ala Asp Ala Ser Glu Thr Met Leu Ala Asn Val Thr Ser Val
 1               5                  10                  15

Arg Gln Glu Tyr Ala Ile
            20

<210> SEQ ID NO 24
<211> LENGTH: 30
<212> TYPE: PRT
<213> ORGANISM: Rotavirus VP6 fragment

<400> SEQUENCE: 24

Gln Glu Tyr Ala Ile Pro Val Gly Pro Val Phe Pro Pro Gly Met Asn
 1               5                  10                  15

Trp Thr Asp Leu Ile Thr Asn Tyr Ser Pro Ser Arg Glu Asp
            20                  25                  30

<210> SEQ ID NO 25
<211> LENGTH: 30
<212> TYPE: PRT
<213> ORGANISM: Rotavirus VP6 fragment
```

```
<400> SEQUENCE: 25

Thr Asp Leu Ile Thr Asn Tyr Ser Pro Ser Arg Glu Asp Asn Leu Gln
1               5                   10                  15

Arg Val Phe Thr Val Ala Ser Ile Arg Ser Met Leu Val Lys
            20                  25                  30
```